United States Patent [19]

Hagen et al.

[11] Patent Number: 5,422,335
[45] Date of Patent: Jun. 6, 1995

[54] HERBICIDES CONTAINING SUBSTITUTED 2-AMINOTHIOPHENES

[75] Inventors: Helmut Hagen, Frankenthal; Gerhard Nilz, Dannstadt-Schauernheim; Helmut Walter, Obrigheim; Andreas Landes, Limburgerhof, all of Germany

[73] Assignee: BASF Aktiengesellschaft, Ludwigshafen, Germany

[21] Appl. No.: 70,389

[22] PCT Filed: Dec. 3, 1991

[86] PCT No.: PCT/EP91/02287

§ 371 Date: Jun. 7, 1993

§ 102(e) Date: Jun. 7, 1993

[87] PCT Pub. No.: WO92/10094

PCT Pub. Date: Jun. 25, 1992

[30] Foreign Application Priority Data

Dec. 13, 1990 [DE] Germany ............ 40 39 734.3

[51] Int. Cl.⁶ .................... A01N 43/12; A01N 47/24; C07D 33/54
[52] U.S. Cl. .................... 504/104; 504/344; 504/348; 504/129; 504/138; 549/57; 549/59; 549/63; 548/564
[58] Field of Search ............ 549/13, 57, 63, 59; 504/129, 141, 148, 149, 288, 104, 344, 289; 548/564

[56] References Cited

U.S. PATENT DOCUMENTS

| | | | |
|---|---|---|---|
| 3,956,315 | 5/1976 | Kobzina | 71/90 |
| 4,137,070 | 1/1979 | Pallos et al. | 504/104 |
| 4,155,744 | 5/1979 | Alt | 71/88 |
| 4,240,820 | 12/1980 | Dickore et al. | 504/289 |
| 4,415,743 | 11/1983 | Martin | 549/491 |
| 4,564,382 | 1/1986 | Liebl et al. | 71/88 |
| 5,035,736 | 7/1991 | Hagen et al. | 504/104 |
| 5,250,505 | 10/1993 | Kast et al. | 549/13 |

FOREIGN PATENT DOCUMENTS 127469 12/1984 European Pat. Off.

OTHER PUBLICATIONS

E. F. Elslager et al., J. Heterocycl. Chem. 9 (1972) 775.
E. C. Taylor et al., J. Org. Chem. 32 (1967) 2, 376.

*Primary Examiner*—Richard L. Raymond
*Assistant Examiner*—Deborah Lambkin
*Attorney, Agent, or Firm*—Keil & Weinkauf

[57] ABSTRACT

A herbicidal composition containing one or more substituted 2-aminothiophenes of the formula I

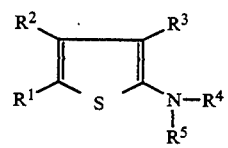

where $R^1$ and $R^2$ together from a $C_4$-alkylene chain to which a benzene ring may be fused, $R^3$ is —CN or $CX$—$R^6$, where $R^6$ is hydroxyl, $C_1$–$C_4$-alkoxy or amino, $R^4$ is hydrogen or a phenyl group which may carry one or two nitro radicals,

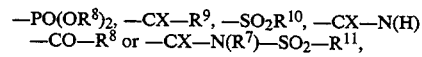

where $R^8$ is hydrogen, $C_1$–$C_4$-alkyl or phenyl group $R^9$ is $C_1$–$C_{20}$-alkyl, partially or completely halogenated $C_1$–$C_6$-alkyl, $C_2$–$C_6$-alkenyl, $C_6$-cycloalkyl, or amino, $C_1$–$C_4$-alkylamino, $C_3$–$C_8$-cycloalkylamino, phenyl or phenylamino, where the aromatic moiety may carry at least one of nitro and halogen;

$R^{10}$ is $C_1$–$C_4$-alkyl or phenyl, which may carry one $C_1$–$C_4$-alkyl radical;

$R^{11}$ is pyrrolidin-1-yl, piperidin-1-yl, morpholin-4-yl or piperazin-1-yl, where the heterocyclic structures may carry one $C_1$–$C_4$-group;

(Abstract continued on next page.)

$R^5$ is hydrogen;

or $R^4$ and $R^5$ together form a group $=CR^{12}R^{13}$ or —CO—W—CO—, where $R^{12}$ is hydrogen, amino, $C_1$–$C_4$-alkylamino or $C_3$–$C_8$-cycloalkylamino;

$R^{13}$ is amino, $C_3$–$C_8$-cycloalkylamino, phenyl or pyridyl, where the two last mentioned substituents may carry at least one halogen or nitro radicals;

W is an ethylene or ethenylene bridge, or a 6-membered 1,2-C-bonded aromatic bridge where these bridge members may carry, on each substitutable carbon atom, at least one halogen a 5-membered or 6-membered 1,2-C-bonded cycloalkylene or cycloalkenylene bridge, and the basic salts of the compounds I in which $R^3$ is hydroxycarbonyl or hydroxythiocarbonyl, and the acidic salts of the compounds I which contain a basic nitrogen atom, as antagonistic compounds and one or more herbicidal active ingredients from the group consisting of the cyclohexenone derivatives of the formula III

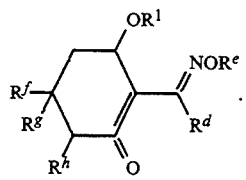

8 Claims, No Drawings

HERBICIDES CONTAINING SUBSTITUTED 2-AMINOTHIOPHENES

The present invention relates to herbicides containing one or more substituted 2-aminothiophenes of the general formula I

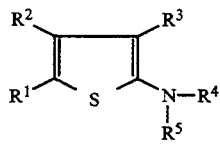

where $R^1$ and $R^2$ are each hydrogen, cyano, $C_1$–$C_4$-alkyl, partially or completely halogenated $C_1$–$C_4$-alkyl or a phenyl group which may carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio, and which may additionally carry a number of halogen atoms so that the total number of radicals is 4 or 5;

—CO—$R^6$ where $R^6$ is hydroxyl, $C_1$–$C_4$-alkyl, $C_1$–$C_4$-alkoxy, $C_1$–$C_4$-alkoxy-$C_1$–$C_4$-alkoxy, amino, $C_1$–$C_4$-alkylamino, di-$C_1$–$C_4$-alkylamino, $C_3$–$C_6$-cycloalkylamino or phenylamino which may carry from one to three halogen, $C_1$–$C_4$-alkyl and/or $C_1$–$C_4$-alkoxy radicals, or $R^1$ and $R^2$ together form a $C_3$–$C_6$-alkylene chain to which a benzene ring may be fused, and this benzene ring may carry from one to three of the following radicals: halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio, and may additionally carry a further halogen atom so that the total number of radicals is 4;

a $C_2$- or $C_3$-alkylene chain which is interrupted by oxygen or by a group —N($R^7$)— and which may carry from one to four $C_1$–$C_4$alkyl radicals, where $R^7$ is hydrogen, phenyl or $C_1$–$C_4$-alkyl;

—CO—N($R^7$)—CO—;

$R^3$ is cyano, —C(NH$_2$)=N-phenyl, where the phenyl radical may carry a halogen atom, or —C(NH$_2$-⊕Hal$^\ominus$)=N-phenyl, where Hal is halogen, or CX—$R^6$, where X is oxygen or sulfur, unless $R^1$ and $R^2$ are CO—$R^6$, $R^4$ is hydrogen, $C_1$–$C_4$-alkyl, $C_2$–$C_4$-alkenyl or a phenyl group which may carry from one to three of the following radicals: nitro, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio, and which may carry a number of halogen atoms so that the total number of radicals is 4 or 5;

a triazine ring which is bonded via a carbon atom and may carry a halogen atom on each of the other two carbon atoms, or —PX(O$R^8$)$_2$, —CX—$R^9$, —SO$_2$$R^{10}$, —SO$_2$—NH$R^{10}$, —CX—N($R^7$)—CY—$R^8$ or —CX—N($R^7$)—SO$_2$—$R^{11}$, where Y is oxygen or sulfur;

$R^8$ is hydrogen, $C_1$–$C_4$-alkyl or a phenyl group which may carry from one to three of the following radicals: $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio;

$R^9$ is $C_1$–$C_{20}$-alkyl, partially or completely halogenated $C_1$–$C_6$-alkyl, $C_2$–$C_6$-alkenyl, partially or completely halogenated $C_2$–$C_6$-alkenyl, $C_3$–$C_6$-cycloalkyl, $C_5$- or $C_6$-cycloalkenyl, where the cyclic radicals may carry a hydroxycarbonyl group, or amino, $C_1$–$C_4$-alkylamino, di-$C_1$–$C_4$-alkylamino, $C_3$–$C_8$-cycloalkylamino, phenyl or phenylamino, where the aromatic moieties may each carry from one to three of the following substituents: nitro, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio, and where the aromatic moieties may each additionally carry a number of halogen atoms so that the total number of radicals is 4 or 5;

$R^{10}$ is $C_1$–$C_4$-alkyl or phenyl, which may carry from one to three of the following radicals: halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio, and which may additionally carry a number of halogen atoms so that the total number of radicals is 4 or 5;

$R^{11}$ is amino, $C_1$–$C_4$-alkylamino, di-$C_1$–$C_4$-alkylamino, pyrrolidin-1-yl, piperidin-1-yl, morpholin-4-yl or piperazin-1-yl, where the heterocyclic structures may carry one or two $C_1$–$C_4$-alkyl groups, or $R^3$ and $R^4$ together form a group —CO—O—CO—;

$R^5$ is hydrogen $C_1$–$C_4$-alkyl, —CX—$R^9$ or —SO$_2$$R^{10}$, or $R^4$ and $R^5$ together form a group =C$R^{12}R^{13}$ or —CO—W—CO—, where $R^{12}$ is hydrogen, amino, $C_1$–$C_4$-alkylamino or $C_3$–$C_8$-cycloalkylamino;

$R^{13}$ is amino, $C_1$–$C_4$-alkylamino, di-$C_1$–$C_4$-alkylamino, $C_3$–$C_8$-cycloalkylamino, thienylamino, where the heteroaromatic may carry a cyano or carbonylamino radical and/or a fused benzene ring, or pyrrolidin-1-yl, piperidin-1-yl, morpholin-4-yl, phenyl or pyridyl, where the two last-mentioned substituents may carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio;

W is an ethylene or ethenylene bridge, a 5-membered or 6-membered 1,2-C-bonded aromatic or heteroaromatic bridge having a nitrogen, oxygen or sulfur atom as a hetero atom, where these bridge members may carry, on each substitutable carbon atom, a radical selected from up to 2 of the following: halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio or partially or completely halogenated $C_1$–$C_4$-alkylthio, and where the bridge members may additionally carry a number of halogen atoms corresponding to the number of further substitutable carbon atoms, or a 5-membered or 6-membered 1,2-C-bonded cycloalkylene or cycloalkenylene bridge, where these substituents may carry from one to four of the following radicals:

halogen or $C_1$–$C_4$-alkyl, and the basic salts of the compounds I in which $R^3$ is hydroxycarbonyl or hydroxythiocarbonyl, and the acidic salts of the compounds I which contain a basic nitrogen atom, as antagonistic compounds and one or more herbicidal active ingredients from the group consisting of A) the 2-(4-hetaryloxy)- or 2-(4-aryloxy)-phenoxyacetic acid derivatives of the formula II

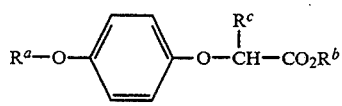

where $R^a$ is phenyl, pyridyl, benzoxazyl, benzothiazyl or benzopyrazinyl, where these aromatic ring systems may carry up to two of the following radicals: halogen, nitro, $C_1$–$C_4$-alkyl, partially or completely halogenated $C_1$–$C_4$-alkyl and/or partially or completely halogenated $C_1$–$C_4$-alkoxy;

$R^b$ is hydrogen, $C_1$–$C_5$-alkyl, $C_3$–$C_5$-alkylideneimino, $C_3$–$C_5$-alkylideneiminooxy-$C_2$- or $C_3$-alkyl or one equivalent of a plant-tolerated cation and $R^c$ is hydrogen or methyl, and B) the cyclohexenone derivatives of the formula III

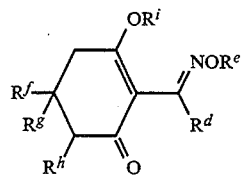

where $R^d$ is $C_1$–$C_4$-alkyl;

$R^e$ is $C_1$–$C_4$-alkyl, $C_3$- or $C_4$-alkenyl, $C_3$- or $C_4$-alkynyl or partially or completely halogenated $C_3$- or $C_4$-alkenyl;

a $C_1$–$C_4$-alkylene or $C_2$–$C_4$-alkenyl chain, both of which may furthermore carry from one to 3 $C_1$–$C_3$-alkyl radicals and/or halogen atoms, or a 3-membered to 6-membered alkylene or 4-membered to 6-membered alkenylene chain which may be substituted by $C_1$–$C_3$-alkyl and each of which contains as a chain member an oxygen or sulfur atom not directly adjacent to the oxime ether moiety, all above-mentioned chains carrying as a terminal group the phenyl ring which in turn may be substituted by from 1 to 3 radicals selected from the group consisting of a benzyloxycarbonyl or phenyl radical and from one to three of each of the following radicals: nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl and $C_1$–$C_4$-alkoxycarbonyl, and it being possible for the phenyl ring additionally to carry a number of halogen atoms such that the total number of radicals is 4 or 5;

thienylmethyl which may carry a halogen atom;

$R^f$ is $C_1$–$C_4$-alkyl which may be monosubstituted by $C_1$–$C_4$-alkylthio or by $C_1$–$C_4$-alkoxy;

a 5-membered or 6-membered saturated or monounsaturated ring system which, in addition to carbon members, may contain an oxygen or sulfur atom or a sulfinyl or sulfonyl group, where this ring may carry up to 3 of the following radicals: hydroxyl, halogen, $C_1$–$C_4$-alkyl, partially or completely halogenated $C_1$–$C_4$-alkyl, $C_1$–$C_4$-alkoxy and/or $C_1$–$C_4$-alkylthio;

a 10-membered saturated or monounsaturated heterocyclic structure which contains two oxygen atoms or sulfur atoms and may be, substituted by up to three $C_1$–$C_4$-alkyl groups and/or methoxy groups;

phenyl, pyridyl, thiazolyl, pyrazolyl, pyrrolyl or isoxazolyl, where these groups may carry from one to three radicals selected from the group consisting of $C_1$–$C_4$-alkyl, partially or completely halogenated $C_1$–$C_4$-alkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-alkylthio-$C_1$–$C_3$-alkyl, $C_1$–$C_4$-dialkoxy-$C_1$–$C_3$-alkyl, formyl, halogen and benzoylamino;

$R^g$ is hydrogen or hydroxyl or, when $R^f$ is $C_1$–$C_6$-alkyl, is $C_1$–$C_6$-alkyl;

$R^h$ is hydrogen, cyano, halogen, $C_1$–$C_4$-alkoxycarbonyl or a group

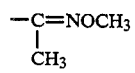

and $R^i$ is hydrogen or one equivalent of an environmentally compatible cation.

The present invention furthermore relates to a method for selectively controlling undesirable plant growth with these herbicides.

Substituted 2-aminothiophenes of the same type as the compounds I are disclosed, inter alia, in the following publications:

EP-A-384 314,

EP-A-385 515,

E. F. Elslager et al., J. Heterocycl. Chem. 9 (1972), 775,

E. C. Taylor et al., J. Org. Chem. 32 (1967), 2376,

K. Gewald, Chem. Ber. 98 (1965), 3571 and

K. Gewald et al., Chem. Ber. 99 (1966), 94.

However, the stated literature does not mention an antagonistic action of the known compounds in combination with herbicidal active ingredients.

On the other hand, EP-A-378 508 discloses 3-aminothiophenes having antidote activity and the following basic structure:

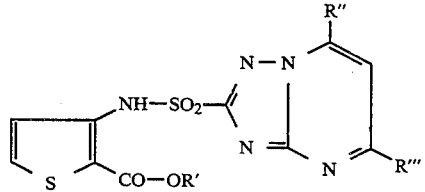

It is an object of the present invention to provide compounds which reduce the disadvantages of using the abovementioned herbicides of the formulae II and III at least to such an extent that the yield of the crops at harvest is no longer reduced or not significantly reduced.

We have found that this object is achieved by the agents defined at the outset.

We have also found methods for the combined treatment of crops with the antidote compounds I on the one hand and the herbicides II and/or III on the other hand, whether the herbicidal active ingredient and the antidote compound are formulated and applied together or separately or, in the case of separate application, the order in which the herbicidal active ingredient and the antidote are applied being unimportant.

Derivatives I having acidic terminal groups or having basic nitrogen atoms may be in the form of their agriculturally useful salts.

Suitable acid addition salts are the salts of acids which do not adversely affect the antidote action of I, for example the hydrochlorides, hydrobromides, sulfates, nitrates, phosphates, oxalates or dodecylbenzenesulfonates.

Suitable basic salts are the salts of bases which do not adversely affect the antidote action of I, for example the alkali metal salts, in particular the sodium and potassium salts, the alkaline earth metal salts, in particular the calcium, magnesium and barium salts, transition metal salts, in particular manganese, copper, zinc and iron salts, ammonium salts which may carry from one to three $C_1$–$C_4$-alkyl or hydroxy-$C_1$–$C_4$-alkyl substituents and/or a phenyl or benzyl substituent, in particular diisopropylammonium, tetramethylammonium, tetrabutylammonium, trimethylbenzylammonium and trimethyl-(2-hydroxyethyl)-ammonium salts, the phosphonium salts, sulfonium salts, in particular tri-$C_1$–$C_4$-alkylsulfonium salts, and the sulfoxonium salts, in particular tri-$C_1$–$C_4$-alkylsulfoxonium salts.

The substituents in the substituted 2-aminothiophenes I have the following specific meanings:

$R^1$ and $R^2$ are each hydrogen;

cyano;

straight-chain or branched $C_1$–$C_8$-alkyl, in particular $C_1$–$C_4$-alkyl, such as methyl, ethyl, n-propyl, isopropyl, n-butyl, isobutyl and tert-butyl, particularly preferably methyl;

straight-chain or branched, partially or completely halogenated $C_1$–$C_4$-alkyl, such as fluoromethyl, difluoromethyl, trifluoromethyl, chloromethyl, trichloromethyl, bromomethyl, pentafluoroethyl and 2-chloro-1,1,2-trifluoroethyl;

phenyl which may carry from one to three of the following radicals:

halogen, such as fluorine, chlorine, bromine and iodine, in particular fluorine or chlorine, nitro, $C_1$–$C_4$-alkyl as stated above, partially or completely halogenated $C_1$–$C_4$-alkyl as stated above, in particular trifluoromethyl, $C_1$–$C_4$-alkoxy, such as methoxy, ethoxy, n-propoxy, isopropoxy, isobutoxy and tert-butoxy, partially or completely halogenated $C_1$–$C_4$-alkoxy, such as fluoromethoxy, difluoromethoxy, trifluoromethoxy, chloromethoxy, dichloromethoxy and trichloromethoxy, in particular chloromethoxy or dichloromethoxy, $C_1$–$C_4$-alkylthio, such as methylthio, ethylthio, n-propylthio, isopropylthio, n-butylthio and tert-butylthio, preferably methylthio or ethylthio, and which may additionally carry a number of halogen atoms so that the total number of radicals is 4 or 5, particularly preferably phenyl or 4-chlorophenyl;

CO—$R^6$, where $R^6$ is hydroxyl, $C_1$–$C_4$-alkyl as stated above, in particular methyl or ethyl, $C_1$–$C_4$-alkoxy as stated above, in particular methoxy or ethoxy, $C_1$–$C_4$-alkoxy-$C_1$–$C_4$-alkoxy, such as methoxymethoxy, ethoxymethoxy, ethoxyethoxy or tert-butoxyethoxy, amino, $C_1$–$C_4$-alkylamino, such as methylamino, ethylamino, n-propylamino, isopropylamino, n-butylamino and tert-butylamino, in particular methylamino or ethylamino, di-$C_1$–$C_4$-alkylamino, such as dimethylamino, diethylamino, methylethylamino or methyl-n-butylamino, $C_3$–$C_6$-cycloalkylamino, such as cyclopropylamino, cyclobutylamino, cyclopentylamino or cyclohexylamino, or phenylamino, where the aromatic moiety may furthermore carry from one to three of the following radicals:

halogen as stated above, such as fluorine or chlorine, $C_1$–$C_4$-alkyl as stated above, and/or $C_1$–$C_4$-alkoxy as stated above, in particular phenylamino;

or $R^1$ and $R^2$ together form a $C_2$–$C_6$-alkylene chain to which a benzene ring may be fused, which benzene ring may carry from one to three of the following radicals: halogen as stated above, in particular fluorine or chlorine, $C_1$–$C_4$-alkyl as stated above, in particular methyl, partially or completely halogenated alkyl as stated above, in particular trifluoromethyl, $C_1$–$C_4$-alkoxy as stated above, in particular methoxy, partially or completely halogenated alkoxy as stated above, in particular trifluoromethoxy, or $C_1$–$C_4$-alkylthio as stated above, in particular methylthio, and where the benzene ring may additionally carry a number of halogen atoms as stated above, in particular fluorine or chlorine, so that the total number of radicals is 4;

a $C_2$- or $C_3$-alkylene chain which is interrupted by oxygen or by a group —$N(R^7)$— and which may carry from one to four $C_1$–$C_4$-alkyl radicals as stated above, in particular methyl, where $R^7$ is hydrogen, phenyl or $C_1$–$C_4$-alkyl as stated above, in particular methyl;

—CO—$N(R^7)$—CO—;

preferred substituents $R^1$ and $R^2$ are hydrogen, cyano or partially or completely halogenated $C_1$–$C_4$-alkyl, and $R^1$ and $R^2$ together form a $C_2$–$C_6$-alkylene chain, the tetramethylene chain being particularly preferred;

$R^3$ is cyano;

—$C(NH_2)$=N-phenyl or —$C(NH_3^{\oplus}Hal^{\ominus})$=N-phenyl, where the phenyl radical in each case may carry a halogen atom as stated above, in particular fluorine or chlorine;

Hal is halogen as stated above, in particular chlorine or bromine;

CX—$R^6$, where X is oxygen or sulfur, unless $R^1$ and $R^2$ are both CO—$R^6$;

a preferred substituent $R^3$ is cyano;

$R^4$ is hydrogen;

$C_1$–$C_4$-alkyl as stated above, in particular methyl or ethyl;

$C_2$–$C_4$-alkenyl, such as ethenyl, prop-2-en-1-yl, but-2-en-1-yl, but-3-en-1-yl or but-3-en-2-yl, in particular ethenyl or prop-2-en-1-yl;

phenyl which may carry from one to three of the following radicals:

nitro;

halogen as stated above, in particular fluorine or chlorine, $C_1$–$C_4$-alkyl as stated above, in particular methyl, partially or completely halogenated alkyl as stated above, in particular trifluoromethyl, $C_1$–$C_4$-alkoxy as stated above, in particular methoxy, partially or completely halogenated $C_1$–$C_4$-alkoxy as stated above, in particular trifluoromethoxy, or $C_1$–$C_4$-alkylthio as stated above, in particular methylthio, and which phenyl group may additionally carry a number of halogen atoms so that the total number of radicals is 4 or 5, particularly preferably phenyl;

a triazine ring which is bonded via a carbon atom and may furthermore carry, on each of the other two carbon atoms, a halogen atom as stated above, in particular fluorine;

—PX(OR$^8$)$_2$, where R$^8$ is hydrogen, C$_1$–C$_4$-alkyl as stated above, in particular methyl, or phenyl which may carry from one to three of the following radicals:

C$_1$–C$_4$-alkyl as stated above, in particular methyl, partially or completely halogenated alkyl as stated above, in particular trifluoromethyl, C$_1$–C$_4$-alkoxy as stated above, in particular methoxy, partially or completely halogenated C$_1$–C$_4$-alkoxy as stated above, in particular trifluoromethoxy, or C$_1$–C$_4$-alkylthio as stated above, in particular methylthio;

—CX—R$^9$, where

X is oxygen or sulfur and

R$^9$ is branched or straight-chain C$_1$–C$_{20}$-alkyl, in particular C$_1$–C$_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

partially or completely halogenated C$_1$–C$_6$-alkyl, in particular C$_1$- or C$_2$-alkyl, such as chloromethyl, dichloromethyl, trichloromethyl, chlorofluoromethyl, fluoromethyl, difluoromethyl, trifluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

C$_2$–C$_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-petenyl, 3-methyl-3-pentenyl, 4-methyl-3-pentenyl, 1-methyl-4-pentenyl, 2-methyl-4-pentenyl, 3-methyl-4-pentenyl, 1-methyl-1-pentenyl, 2-methyl-4-pentenyl, 3-methyl-4-pentenyl, 4-methyl-4-pentenyl, 1,1-dimethyl-2-butenyl, 1,1-di-methyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, in particular prop-2-en-1-yl;

partially or completely halogenated C$_2$–C$_6$-alkenyl, such as 2-fluoroethenyl, 2-chloroethenyl, trifluoroethenyl, trichloroethenyl and 2-chloroprop-2-en-1-yl;

C$_3$–C$_6$-cycloalkyl, such as cyclopropyl, cyclobutyl, cyclopentyl and cyclohexyl, where these radicals may carry a hydroxycarbonyl group;

C$_5$- or C$_6$cycloalkenyl, such as cyclopent-1-en-1-yl, cyclopent-2-en-1-yl, cyclopent-3-en-1-yl, cyclohex-1-en-1-yl, cyclohex-2-en-1-yl and cyclohex-3-en-1-yl, where these radicals may carry a hydroxycarbonyl group;

amino;

C$_1$–C$_4$-alkylamino, such as methylamino, ethylamino, n-propylamino, isopropylamino, n-butylamino and tert-butylamino, in particular methylamino or ethylamino;

di-C$_1$–C$_4$-alkylamino, such as N,N-dimethylamino, N,N-diethylamino, N,N-dipropylamino, N,N-di-(1-methylethyl)-amino, N,N-dibutylamino, N,N-di-(1-methylpropyl)-amino, N,N-di-(2-methylpropyl)-amino, N,N-di-(1,1-dimethylethyl)-amino, N-ethyl-N-methylamino, N-methyl-N-propylamino, N-methyl-N-(1-methylethyl)-amino, N-butyl-N-methylamino, N-methyl-N-(1-methylpropyl)-amino, N-methyl-N-(2-methylpropyl)-amino, N-(1,1-dimethylethyl)-N-methylamino, N-ethyl-N-propylamino, N-ethyl-N-(1-methylethyl)-amino, N-butyl-N-ethylamino, N-ethyl-N-(1-methylpropyl)-amino, N-ethyl-N-(2-methylpropyl)-amino, N-ethyl-N-(1,1-dimethylethyl)-amino, N-(1-methylethyl)-N-propylamino, N-butyl-N-propylamino, N-(1-methylpropyl)-N-propylamino, N-(2-methylplropyl)-N-propylamino[sic], N-(1,1-dimethylethyl)-N-propylamino, N-butyl-N-(1-methylethyl)-amino, N-(1-methylethyl)-N-(1-methylpropyl)-amino, N-(1-methylethyl)-N-(2-methylpropyl)-amino, N-(1,1-dimethylethyl)-N-(1-methylethyl)-amino, N-butyl-N-(1-methylpropyl)-amino, N-butyl-N-(2-methylpropyl)-amino, N-butyl-N-(1,1-dimethylethyl)-amino, N-(1-methylpropyl)-N-(2-methylpropyl)-amino, N-(1,1-dimethylethyl)-N-(1-methylpropyl)-amino and N-(1,1-dimethylethyl)-N-(2-methylpropyl)-amino;

C$_3$–C$_8$-cycloalkylamino, such as cyclopropylamino, cyclobutylamino, cyclopentylamino, cyclohexylamino, cycloheptylamino and cyclooctylamino, in particular cyclopropylamino;

phenyl or phenylamino, where the aromatic moiety in turn may carry up to three of the following radicals: nitro, halogen as stated above, in particular fluorine or chlorine, C$_1$–C$_4$-alkyl as stated above, partially or completely halogenated C$_1$–C$_4$-alkyl as stated above, in particular trifluoromethyl or trichloromethyl, C$_1$–C$_4$-alkoxy as stated above, in particular methoxy or ethoxy, partially or completely halogenated C$_1$–C$_4$-alkoxy as stated above, in particular trifluoromethoxy or trichloromethoxy, or C$_1$–C$_4$-alkylthio as stated above, in particular methylthio, and where each aromatic moiety may carry a number of halogen atoms as stated above, in particular fluorine or chlorine, so that the total number of radicals is 4 or 5;

R$^{10}$ is C$_1$–C$_4$-alkyl as stated above or phenyl which may carry from one to three of the following radicals: halogen as stated above, in particular fluorine or chlorine, nitro, C$_1$–C$_4$-alkyl as stated above, partially or completely halogenated C$_1$–C$_4$-alkyl as stated above, in particular trifluoromethyl, C$_1$–C$_4$-alkoxy as stated above, partially or completely halogenated C$_1$–C$_4$-alkoxy as stated above, in particular methoxy or ethoxy, C$_1$–C$_4$-alkylthio as stated above, in particular methylthio, where the phenyl group may additionally carry a number of halogen atoms as stated above, in particular fluorine or chlorine, so that the total number of radicals is 4 or 5;

$R^{11}$ is amino;

$C_1$–$C_4$-alkylamino as stated above, in particular methylamino or ethylamino;

di-$C_1$–$C_4$-alkylamino as stated above, in particular dimethylamino or diethylamino;

pyrrolidin-1-yl, piperidin-1-yl, morpholin-4-yl or piperazin-1-yl, where the heterocyclic structures may carry one or two $C_1$–$C_4$-alkyl groups as stated above; or $R^3$ and $R^4$ together form a group —CO—O—CO—;

$R^5$ is hydrogen;

$C_1$–$C_4$-alkyl as stated above or —CX—$R^9$ or —SO$_2$—$R^{10}$, where the variables have the above-mentioned meanings, or $R^4$ and $R^5$ together form a group =$CR^{12}R^{13}$ or —CO—W—CO—, where $R^{12}$ is hydrogen, amino, $C_1$–$C_4$-alkylamino as stated above, in particular methylamino or ethylamino, or $C_3$–$C_8$-cycloalkylamino, such as cyclopropylamino, cyclobutylamino, cyclopentylamino, cyclohexylamino, cycloheptylamino and cyclooctylamino, in particular cyclopropylamino, cyclopentylamino or cyclohexylamino;

$R^{13}$ is amino, $C_1$–$C_4$-alkylamino as stated above, in particular methylamino or ethylamino, di-$C_1$–$C_4$-alkylamino as stated above, in particular dimethylamino or diethylamino, $C_3$–$C_8$-cycloalkylamino as stated above, in particular cyclopropylamino, cyclopentylamino or cyclohexylamino, pyrrolidin-1-yl, piperidin-1-yl, morpholin-4-yl, phenyl or pyridyl, where the two last-mentioned substituents may carry from one to three of the following radicals:

halogen as stated above, in particular fluorine or chlorine, nitro, $C_1$–$C_4$-alkyl as stated above, in particular methyl, ethyl, isopropyl or tert-butyl, partially or completely halogenated $C_1$–$C_4$-alkyl as stated above, in particular trifluoromethyl, $C_1$–$C_4$-alkoxy as stated above, in particular methoxy or ethoxy, partially or completely halogenated $C_1$–$C_4$-alkoxy as stated above, in particular trifluoromethoxy, and/or $C_1$–$C_4$-alkylthio as stated above, in particular methylthio, particularly preferably phenyl, 4-ethoxyphenyl or pyrid-2-yl;

W is an ethylene or ethenylene bridge, a 5-membered or 6-membered 1,2-C-bonded aromatic or heteroaromatic bridge having a nitrogen, oxygen or sulfur atom as a hetero atom, where these bridge members may carry, on each substitutable carbon atom, a radical selected from up to 2 of the following: halogen as stated above, in particular fluorine or chlorine, $C_1$–$C_4$-alkyl as stated above, in particular methyl or tert-butyl, partially or completely halogenated $C_1$–$C_4$-alkyl as stated above, in particular trifluoromethyl, $C_1$–$C_4$-alkoxy as stated above, in particular methoxy, partially or completely halogenated $C_1$–$C_4$-alkoxy as stated above, in particular trifluoromethoxy, $C_1$–$C_4$-alkylthio as stated above, in particular methylthio, and/or partially or completely halogenated $C_1$–$C_4$-alkylthio, such as fluoromethylthio, chloromethylthio, bromomethylthio, trichloromethylthio, trifluoromethylthio and pentafluoroethylthio, in particular trifluoromethylthio, and where the bridge members may carry a number of halogen atoms as stated above, in particular fluorine or chlorine, equivalent to the number of further substitutable carbon atoms in the aromatic moiety, particularly preferably

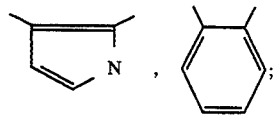

or a 5-membered or 6-membered 1,2-C-bonded cycloalkylene or cycloalkenylene bridge, such as cyclopentylidene, cyclohexylidene, cyclopentenylidene and cyclohexenylidene, where these substituents may carry from one to four halogen atoms as stated above, in particular fluorine or chlorine, and/or $C_1$–$C_4$-alkyl groups as stated above, in particular methyl, particularly preferably

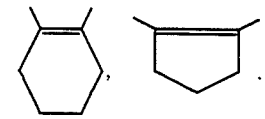

The substituted 2-aminothiophenes of the formula I are obtainable by various methods, preferably by one of the following processes:

a) Condensation of a ketone XI with sulfur and an acetonitrile derivative XII to give a substituted 2-aminothiophene Ia:

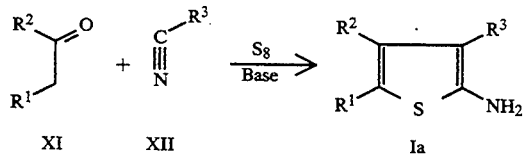

The reaction is carried out in general in a conventional manner [cf. K. Gewald et al., Chem. Ber. 99 (1966), 94 and E. F. Elslager et al., J. Heterocycl. Chem. 9 (1972) 775] in an inert solvent or diluent, for example in an alcohol, such as methanol, ethanol, n-propanol and isopropanol, in an ether, such as dioxane and tetrahydropyran, in a nitrile, such as acetonitrile and propionitrile, in an aprotic solvent, such as dimethylformamide, dimethyl sulfoxide and N-methylpyrrolidone, or in an excess of the ketone XI.

The reaction can also be carried out using a phase transfer catalyst, such as trioctylpropylammonium chloride and cetyltrimethylammonium chloride, in a 2-phase system of water and a hydrocarbon, e.g. carbon tetrachloride [cf. Synthesis (1974) 867].

The reaction is preferably carried out in the presence of an inorganic or organic base.

Examples of suitable bases are alkali metal hydroxides, such as sodium hydroxide and potassium hydroxide, alkaline earth metal hydroxides, such as calcium hydroxide, alkaline earth metal alcoholates, such as sodium methylate, sodium ethylate, potassium ethylate and potassium tert-butylate, alkaline earth metal alcoholates, such as a calcium alcoholate, alkali metal hydrides, such as sodium hydride and potassium hydride, alkaline earth metal hydrides, such as calcium hydride, aliphatic amines, such as dimethylamine, triethylamine and diisopropylamine, dimethylaniline, dimethylbenzylamine, piperidine and heteroaromatic amines, such as pyridine and 4-dimethylaminopyridine.

In the case of the amines, the reaction can also be carried out in an excess of base, in the absence of a solvent.

All reactants are advantageously used in stoichiometric amounts, but it is also possible to use an excess of up to about 10 mol % of one or other component.

If the base is used as the solvent, it is present in a large excess.

In general, the reaction temperature is from 0° to 200° C., preferably from 20° to 140° C., in particular at the boiling point of the relevant solvent.

The reaction is usually carried out at atmospheric pressure or at the autogenous pressure of the solvent used.

Other possible methods of synthesis comprise reacting α-mercaptoketones with acetonitrile derivatives XII having an active methylene group [cf. K. Gewald, Chem. Ber. 98 (1965), 3571].

b) The reaction of substituted 2-aminothiophenes Ia with an electrophilic compound XIII to XVIII:

carried out in a 2-phase system of water and a hydrocarbon, e.g. carbon tetrachloride.

Regarding the bases and phase transfer catalysts which can be used, the ratios and the pressure, the data given for method (a) are applicable.

In general, the reaction temperature is from 0° to 200° C., preferably from 20° to 140° C., in particular the boiling point of the relevant solvent.

The electrophilic compounds XIII to XVIII are known or are obtainable by known processes (cf. Sustmann in Houben-Weyl: Methoden der Organischen Chemie, Volume E5, 590–608 and 634–652). The educts XVIa and XVIb are advantageously prepared in situ from halosulfonyl isocyanates and reactive compounds $R^{11}$-H and the compounds XVIIa and XVIIb are prepared in a similar manner from isocyanate salts, such as ammonium isocyanate and compounds Hal—CY—$R^8$.

The substituted 2-aminothiophenes I are suitable as antidotes for increasing the toleration of herbicidal active ingredients by crops such as millet, rice, corn, cereals (wheat, rye, barley and oats), cotton, sugar beet, sugar cane and soybean. They have an antagonistic effect on herbicides of a very wide range of classes,

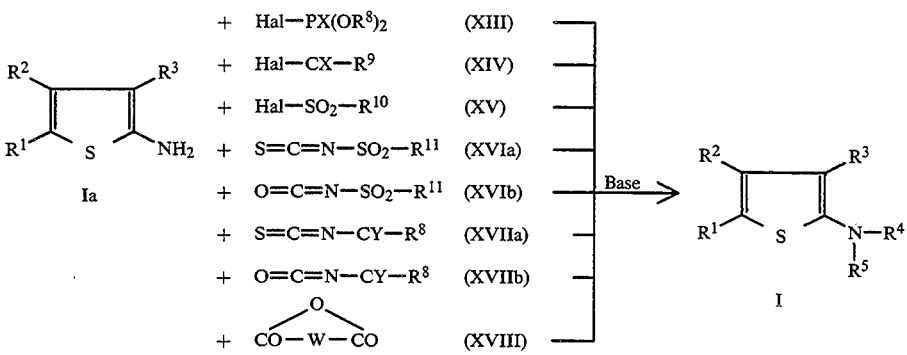

Hal is chlorine or bromine.

The reactions are usually carried out by conventional processes in an inert solvent or diluent in the presence of a base:

for the reaction of Ia with carbonyl halides or anhydrides to give amides or imides, respectively, see Henecka in Houben-Weyl, Methoden der Organischen Chemie, Volume 8, pages 653–713;

for the reaction of Ia with sulfonyl chlorides to give sulfonamides, see Mutz in Houben-Weyl, Methoden der Organischen Chemie, Volume 9, pages 599–658;

for the reaction of Ia with iso(thio)cyanates to give (thio)ureas, see Petersen in Houben-Weyl, Methoden der Organischen Chemie, Volume 8, pages 129–136;

for the reaction of Ia with aromatic aldehydes to give Schiff bases, see Freytag in Houben-Weyl, Volume 11/2, pages 73–98.

Examples of suitable solvents are aliphatic hydrocarbons, such as n-hexane, gasoline and petroleum ether, aromatic hydrocarbons, such as benzene, toluene, and o-, m- and p-xylene, chlorohydrocarbons, such as dichloromethane, chloroform, tetrachloromethane, 1,2-dichloroethane and chlorobenzene, nitrogen-containing heteroaromatics, such as pyridine and quinoline, cyclic ethers, such as tetrahydrofuran and dioxane, nitriles, such as acetonitrile and propionitrile, and dimethylformamide, dimethyl sulfoxide and N-methylpyrrolidone, or a mixture of the stated solvents. In the presence of a phase transfer catalyst, the reaction can also be such as triazines, phenylurea derivatives, carbamates, thiocarbamates, haloacetanilides, benzoic acid derivatives and in particular halophenoxyacetic esters, substituted phenoxyphenoxyacetic esters, phenoxyphenoxypropionic esters and cyclohexenone derivatives.

Herbicidal active ingredients from the group consisting of the 2-(4-hetaryloxy)- or 2-(4-aryloxy)phenoxyacetic acid derivatives of the formula II

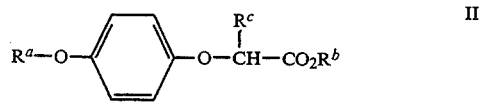

where $R^4$ is phenyl, pyridyl, benzoxazyl, benzothiazyl or benzopyrazinyl, where these aromatic ring systems may carry up to two of the following radicals: halogen, nitro, $C_1$-$C_4$-alkyl, $C_1$-$C_4$-haloalkyl and/or $C_1$-$C_4$-haloalkoxy;

$R^b$ is hydrogen, $C_1$-$C_4$-alkyl or one equivalent of a plant-tolerated cation and $R^c$ is hydrogen or methyl, are disclosed in the literature, for example in DE-A-22 23 894, DE-A-24 33 067, DE-A-25 76 251, DE-A-30 04 770, BE-A-868 875 and BE-A-858 618.

They are used for controlling undesirable plants from the Gramineae family. However, the toleration of these substances by crops varies from commercially acceptable to non-tolerated, depending on the substituents and the application rate.

The same applies to cyclohexenone derivatives of the formula III

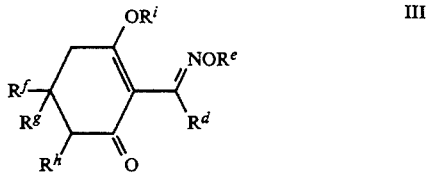

where $R^d$ is $C_1$–$C_4$-alkyl which [lacuna] methyl, ethyl, n-propyl, isopropyl, n-butyl and tert-butyl, preferably ethyl and n-propyl;

$R^e$ is $C_1$–$C_4$-alkyl, such as methyl, ethyl, n-propyl, isopropyl, n-butyl and tert-butyl, preferably ethyl or n-propyl, $C_3$- or $C_4$-alkenyl, preferably prop-2-enyl, $C_3$- or $C_4$-alkynyl or $C_3$- or $C_4$-haloalkenyl, preferably 3-chloroprop-2-en-1-yl, a $C_1$–$C_4$- alkylene or $C_2$–$C_4$-alkenylene chain, both of which may furthermore carry from one to three $C_1$–$C_3$-alkyl radicals and/or halogen atoms, or a 3-membered to 6-membered alkylene or 4-membered to 6-membered alkenylene chain which may be substituted by $C_1$–$C_3$-alkyl and each of which contains as a chain member an oxygen or sulfur atom not directly adjacent to the oxime ether moiety, all abovementioned chains carrying as a terminal group the phenyl ring which in turn may be substituted by from one to three radicals selected from the group consisting of a benzyloxycarbonyl or phenyl radical and from one to three of each of the following radicals:

nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl and $C_1$–$C_4$-alkoxycarbonyl, and it being possible for the phenyl ring additionally to carry a number of halogen atoms such that the total number of radicals is 4 or 5; 4-(p-fluorophenyl)-but-3-enyl, 4-(p-chlorophenyl)-but-3-enyl and 2-(p-chlorophenoxy)-propyl are particularly preferred;

thienyl which may carry a halogen atom;

$R^f$ is $C_1$–$C_4$-alkyl as stated for $R^d$, which may be monosubstituted or disubstituted by $C_1$–$C_4$-alkylthio or by $C_1$–$C_4$-alkoxy, a 5-membered or 6-membered saturated or monounsaturated ring system which, in addition to carbon members, may contain an oxygen or sulfur atom or a sulfinyl or sulfonyl group, preferably tetrahydropyranyl, dihydropyranyl and tetrahydrothiopyranyl, where the ring system may carry from one to three radicals selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio, a 10-membered saturated or monounsaturated heterocyclic structure which contains two nonadjacent oxygen atoms or sulfur atoms and may be substituted by up to three $C_1$–$C_4$-alkyl groups and/or methoxy groups, or phenyl, pyridyl, thiazolyl, pyrazolyl, pyrrolyl or isoxazolyl, where each of these groups may carry from one to three radicals selected from the group consisting of: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and benzoylamino;

$R^g$ is hydrogen or hydroxyl or, when $R^f$ is $C_1$–$C_6$-alkyl, is $C_1$–$C_6$-alkyl, preferably hydrogen;

$R^h$ is hydrogen, cyano, halogen, $C_1$–$C_4$-alkoxycarbonyl or a $C_1$–$C_4$-alkylketoxime group, preferably hydrogen;

$R^i$ is hydrogen or one equivalent of an agriculturally useful cation.

They are also described in the literature (e.g. EP-A 228 598, EP-A 230 235, EP-A 238 021, EP-A 368 227, U.S. Pat. No. 4,432,786, DE-A 24 39 104, DE-A 40 14 986 and DE-A 40 33 423) as herbicides and are used predominantly for controlling undesirable grasses in dicotyledon crops and in grasses which do not belong to the Gramineae family. Depending on the structure of the substituents and the dose used, compounds of this group can also be used for selectively controlling undesirable grasses in gramineous crops such as wheat and rice.

Cyclohexenone derivatives of the formula III in which $R^e$ is an unsubstituted or substituted alkylphenyl or alkenylphenyl radical, e.g. butyl- or butenylphenyl, can be prepared in a conventional manner from already known derivatives of the formula IV (EP-A 80 301, EP-A 125 094, EP-A 142 741, U.S. Pat. No. 4,249,937, EP-A 137 174 and EP-A 177 913) and the corresponding hydroxylamines of the formula V (Houben-Weyl, 10/1, page 1181 et seq.) (EP-A 169 521).

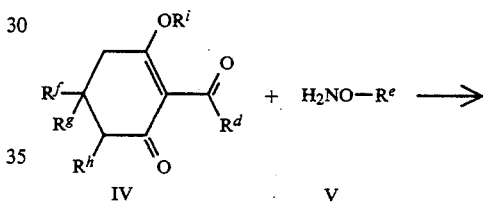

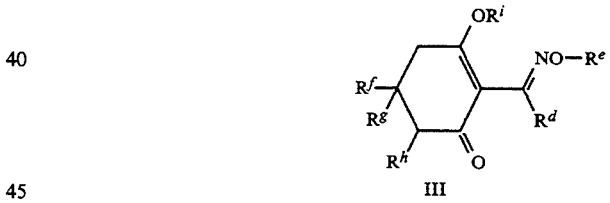

The reaction is advantageously carried out in the heterogeneous phase in a solvent at a sufficient temperature below about 80° C., in the presence of a base, and the hydroxylamine V is used in the form of its ammonium salt.

Examples of suitable bases are carbonates, bicarbonates, acetates, alcoholates or oxides of alkali or alkaline earth metals, in particular sodium hydroxide, potassium hydroxide, magnesium oxide and calcium oxide. Organic bases, such as pyridine or tertiary amines, may also be used. The base is added, for example, in an amount of from 0.5 to 2 mol equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The product can be isolated, for example, by evaporating down the mixture, partitioning the residue in methylene chloride/water and distilling off the solvent under reduced pressure.

However, it is also possible to use the free hydroxylamine base directly, for example in the form of an aqueous solution, for this reaction; depending on the solvent used for the compound IV, a one-phase or two-phase reaction mixture is obtained.

Examples of suitable solvents for this version are alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds III can be obtained by treating the 3-hydroxy compounds with sodium hydroxide, potassium hydroxide or a sodium or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts, by means of ammonia or ammonium, phosphonium, sulfonium or sulfoxonium hydroxides.

The compounds of type IV can be prepared by known methods (Tetrahedron Lett. (1975), 2491), for example from the corresponding cyclohexane-1,3-diones of the formula VI

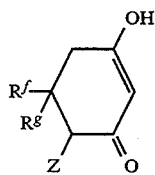

VI where Z is hydrogen or methoxycarbonyl and $R^g$ is hydrogen.

It is also possible to prepare the compounds of the formula IV via the enol ester intermediates, which are obtained in the reaction of compounds of the formula VI with acyl chlorides in the presence of a base and are then subjected to a rearrangement reaction with certain imidazole or pyridine derivatives (Japanese Preliminary Published Application 79/063 052).

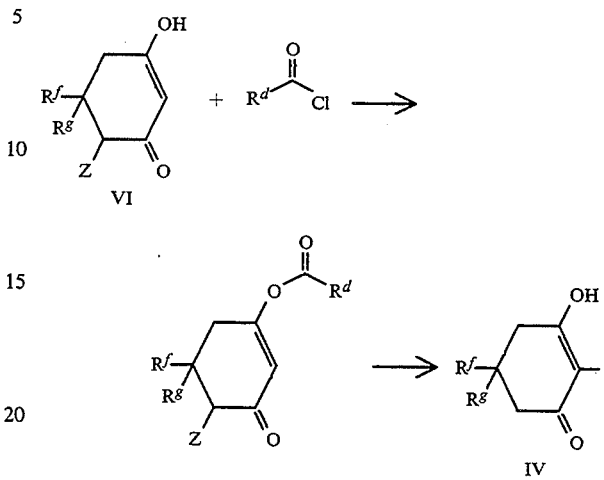

The compounds of the formula VI are obtained by a number of known process steps, starting from known intermediates.

The hydroxylamines V in which $R^e$ is unsubstituted or substituted phenylbutyl are synthesized according to the reaction scheme below, for example via A) alkylation of cyclic hydroxyimides VII with suitable phenylbutyl halides and subsequent elimination of the protective group, for example with hydrazine or ethanolamine, similarly to Examples from EP-A-244 786 or Houben-Weyl, Methoden der organischen Chemie, Volume X/1, page 152 et seq.

B) Hydrogenation of N-4-phenylbutenyloxyphthalimides, whose preparation is described in DE-A 38 38 310, by means of suitable catalysts, e.g. palladium on active carbon, in suitable inert solvents, such as methanol, tetrahydrofuran or dioxane, and subsequent elimination of the protective group as described above.

The hydrogenation is advantageously carried out at 20° C. to the boiling point of the solvent, in particular at room temperature, by a conventional method, at atmospheric, superatmospheric or reduced pressure. A pressure range of from 1 to 10, in particular from 1 to 2, bar is preferred.

Reaction scheme:

Route a)

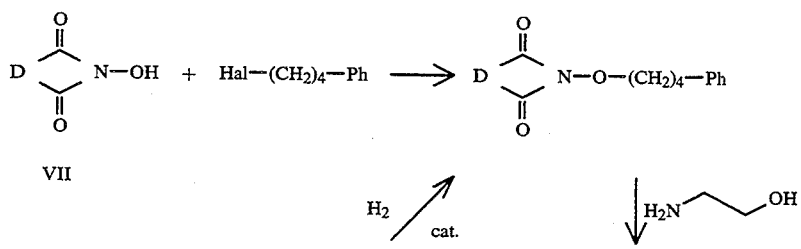

Route b)

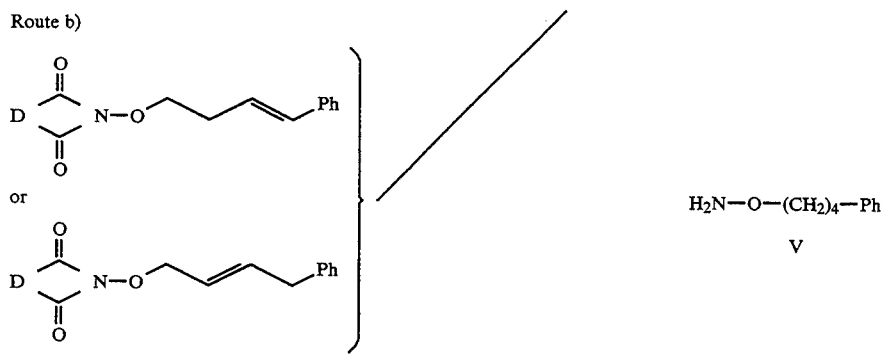

Ph = unsubstituted or substituted phenyl

Examples of suitable cyclic hydroxyimides VII are the following substances:

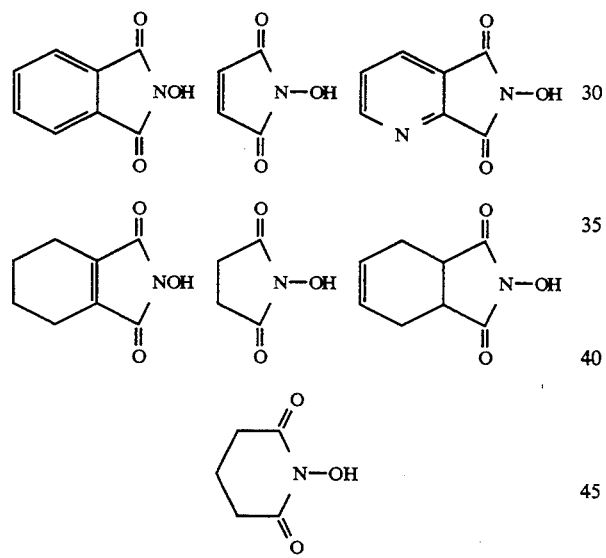

The synthesis of the hydroxylamines V in which $R^e$ is unsubstituted or substituted butenylphenyl, where the phenyl radical abbreviated to Ph below may in turn be substituted or unsubstituted, is carried out according to the reaction scheme below, by diazotization of aniline derivatives and subsequent coupling of the diazonium salt to a correspondingly substituted butadiene VIII. The resulting mixture IXa and IXb is coupled to a cyclic hydroxyimide XI, and the resulting protected hydroxylamine derivative X is cleaved with 2-aminoethanol to give the free hydroxylamine V:

Route c)

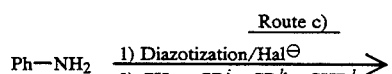

IXa

-continued
Route c)

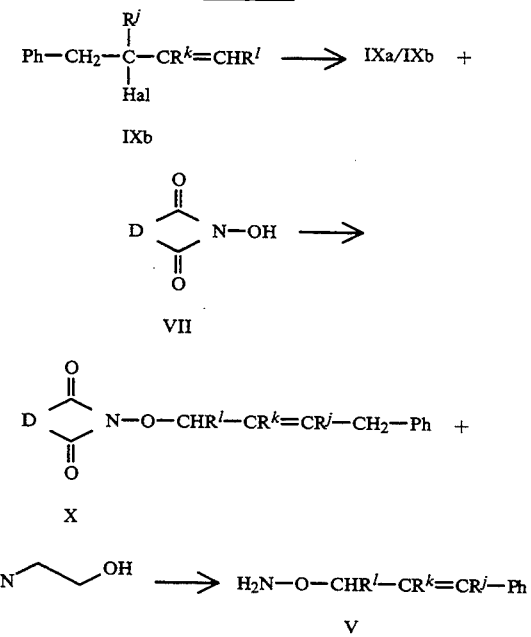

$R^j$, $R^k$ and $R^l$ independently of one another are each hydrogen, $C_1$-$C_3$-alkyl and/or halogen. Hal is halogen, preferably chlorine.

The halides IXa required for the above synthesis of the hydroxylamines V can be prepared, as a mixture with IXb, by processes known from the literature, for example by reacting diazonium salts of aromatic and heteroaromatic anilines with dienes. The range of use of the reaction is discussed in Organic Reactions 11 (1960), 189 and ibid. 24 (1976), 225.

Coupling of the isomeric halides IXa and IXb to a cyclic hydroxyimide of the formula VII gives exclusively the cyclic imido ethers of the formula X which, after elimination of the protective group on the nitrogen, give the hydroxylamines V.

The reaction with a hydroxyimide VII (Routes a and c) is carried out in the presence of an acid acceptor and of a solvent. For cost reasons, hydroxyphthalimide is preferably used as the hydroxyimide VII.

Suitable acid acceptors are alkali metal carbonates, such as potassium carbonate or sodium carbonate, alkali metal bicarbonates, such as potassium bicarbonate and sodium bicarbonate, tertiary amines, such as trimethylamine and triethylamine, and basic heterocycles, such as pyridine. For cost reasons, potassium carbonate and sodium carbonate are preferred.

Suitable solvents are aprotic dipolar organic solvents, e.g. dimethylformamide, dimethyl sulfoxide and/or sulfolane.

Alkylation under phase transfer conditions is also possible. Water-immiscible compounds, such as hydrocarbons or chlorohydrocarbons, are used here as organic solvents. Suitable phase transfer catalysts are quaternary ammonium and phosphonium salts.

The cleavage of the cyclic imido ethers X is carried out similarly to a process described in EP-A 244 786, using an alkanolamine. In this process, the hydroxylamines V can be isolated as free bases or, after precipitation with acids, as salts. Readily crystallizing salts are obtained by reacting the bases with oxalic acid.

The specific examples of herbicidal (hetaryloxy)- and aryloxyphenoxyacetic acid derivatives of the formula II whose toleration by crops can be improved by substituted 2-aminothiophenes I are shown in Table 1 below.

TABLE 1

$R^a$—O—⟨phenyl⟩—O—CH($R^c$)—CO$_2R^b$  II

| No. | $R^a$ | $R^b$ | $R^c$ | Reference |
|---|---|---|---|---|
| 1.1 | 3,4-dichlorophenyl | CH$_3$ | CH$_3$ | DE-A 22 23 894 |

TABLE 1-continued $R^a$—O—⟨phenyl⟩—O—CH($R^c$)—CO$_2R^b$  II

| No. | $R^a$ | $R^b$ | $R^c$ | Reference |
|---|---|---|---|---|
| 1.2 | 5-trifluoromethylpyridin-2-yl | n-C$_4$H$_9$ | CH$_3$ | BE-A 868 875 |
| 1.3 | 6-chloro-benzoxazol-2-yl | C$_2$H$_5$ | CH$_3$ | BE-A 858 618 |
| 1.4 | 3-chloro-5-trifluoromethylpyridin-2-yl | CH$_3$ | CH$_3$ | BE-A 868 875 |
| 1.5 | 7-chloroquinoxalin-2-yl | C$_2$H$_5$ | CH$_3$ | DE-A 30 04 770 |

Specific examples of herbicidal cyclohexenones of the formula II whose toleration by crops can be improved by substituted 2-aminothiophenes I are shown in Tables 2 to 13 below.

TABLE 2

$R^f$—⟨cyclohexenone with OH, NO—CH$_2$CH$_2$O—phenyl(Radicals), =O, $R^d$⟩

III ($R^e$ = —CH$_2$CH$_2$—O—⟨phenyl⟩Radicals ; $R^g$, $R^h$, $R^i$ = H)

| No. | $R^d$ | $R^f$ | Radicals on phenyl ring | Phys. data/ $^1$H-NMR [δ in ppm], mp. [°C.] |
|---|---|---|---|---|
| 2.01 | Ethyl | Tetrahydropyran-3-yl | — | 42–45 |
| 2.02 | Propyl | Tetrahydropyran-3-yl | — | 3,90 (m, 2H), 4,20 (t, 2H), 4,40 (m, 2H), 6,80–7,00 (m, 3H), 7,13–7,37 (m, 2H) |
| 2.03 | Ethyl | Tetrahydropyran-4-yl | — | 106–107 |
| 2.04 | Propyl | Tetrahydropyran-4-yl | — | 72–73 |
| 2.05 | Ethyl | Tetrahydrothiopyran-3-yl | — | 52–55 |
| 2.06 | Propyl | Tetrahydrothiopyran-3-yl | — | 92 |
| 2.07 | Ethyl | Tetrahydropyran-3-yl | 2-F | 76–78 |
| 2.08 | Propyl | Tetrahydropyran-3-yl | 2-F | 72–77 |
| 2.09 | Ethyl | Tetrahydropyran-4-yl | 2-F | 121–125 |
| 2.10 | Propyl | Tetrahydropyran-4-yl | 2-F | 103–107 |
| 2.11 | Ethyl | Tetrahydrothiopyran-3-yl | 2-F | 82–86 |
| 2.12 | Propyl | Tetrahydrothiopyran-3-yl | 2-F | 81–85 |
| 2.13 | Ethyl | Tetrahydropyran-3-yl | 3-F | 62–68 |
| 2.14 | Propyl | Tetrahydropyran-3-yl | 3-F | 3,90 (m, 2H), 4,20 (t, 2H), 4,40 (m, 2H) 6,70 (m, 3H), 7,25 (m, 1H), |
| 2.15 | Ethyl | Tetrahydropyran-4-yl | 3-F | 103–109 |
| 2.16 | Propyl | Tetrahydropyran-4-yl | 3-F | 73–79 |
| 2.17 | Ethyl | Tetrahydrothiopyran-3-yl | 3-F | 4,20 (t, 2H), 4,40 (m, 2H) 6,70 (m, 3H), 7,25 (m, 1H) |
| 2.18 | Propyl | Tetrahydrothiopyran-3-yl | 3-F | |
| 2.19 | Ethyl | Tetrahydropyran-3-yl | 4-F | 64–67 |
| 2.20 | Propyl | Tetrahydropyran-3-yl | 4-F | 70–72 |
| 2.21 | Ethyl | Tetrahydropyran-4-yl | 4-F | 101–103 |
| 2.22 | Propyl | Tetrahydropyran-4-yl | 4-F | 107–109 |
| 2.23 | Ethyl | Tetrahydrothiopyran-3-yl | 4-F | 105–108 |
| 2.24 | Propyl | Tetrahydrothiopyran-3-yl | 4-F | 82–84 |

TABLE 2-continued

III ($R^e = -CH_2CH_2-O-$⟨phenyl⟩-Radicals ; $R^g, R^h, R^i = H$)

| No. | $R^d$ | $R^f$ | Radicals on phenyl ring | Phys. data/ $^1$H-NMR [δ in ppm], mp. [°C.] |
|---|---|---|---|---|
| 2.25 | Ethyl | Tetrahydropyran-3-yl | 2-Cl | 74–80 |
| 2.26 | Propyl | Tetrahydropyran-3-yl | 2-Cl | 67–71 |
| 2.27 | Ethyl | Tetrahydropyran-4-yl | 2-Cl | 4,00 (m, 2H), 4,27 (t, 2H), 4,47 (m, 2H), 7,20 (t, 1H), 7,37 (d, 1H) |
| 2.28 | Propyl | Tetrahydropyran-4-yl | 2-Cl | 68–72 |
| 2.29 | Ethyl | Tetrahydrothiopyran-3-yl | 2-Cl | 74–78 |
| 2.30 | Propyl | Tetrahydrothiopyran-3-yl | 2-Cl | 72–78 |
| 2.31 | Ethyl | Tetrahydropyran-3-yl | 3-Cl | |
| 2.32 | Propyl | Tetrahydropyran-3-yl | 3-Cl | |
| 2.33 | Ethyl | Tetrahydropyran-4-yl | 3-Cl | |
| 2.34 | Propyl | Tetrahydropyran-4-yl | 3-Cl | |
| 2.35 | Ethyl | Tetrahydrothiopyran-3-yl | 3-Cl | |
| 2.36 | Propyl | Tetrahydrothiopyran-3-yl | 3-Cl | |
| 2.37 | Ethyl | Tetrahydropyran-3-yl | 4-Cl | 3,93 (m, 2H), 4,20 (t, 2H), 4,43 (m, 2H), 6,90 (m, 2H), 7,25 (m, 2H) |
| 2.38 | Propyl | Tetrahydropyran-3-yl | 4-Cl | 3,93 (m, 2H), 4,20 (t, 2H), 4,43 (m, 2H), 6,90 (m, 2H), 7,25 (m, 2H) |
| 2.39 | Ethyl | Tetrahydropyran-4-yl | 4-Cl | 116–118 |
| 2.40 | Propyl | Tetrahydropyran-4-yl | 4-Cl | 104–106 |
| 2.41 | Ethyl | Tetrahydrothiopyran-3-yl | 4-Cl | 74–77 |
| 2.42 | Propyl | Tetrahydrothiopyran-3-yl | 4-Cl | 86–88 |
| 2.43 | Ethyl | Tetrahydropyran-3-yl | 2-$CF_3$ | |
| 2.44 | Propyl | Tetrahydropyran-3-yl | 2-$CF_3$ | |
| 2.45 | Ethyl | Tetrahydropyran-4-yl | 2-$CF_3$ | |
| 2.46 | Propyl | Tetrahydropyran-4-yl | 2-$CF_3$ | |
| 2.47 | Ethyl | Tetrahydrothiopyran-3-yl | 2-$CF_3$ | |
| 2.48 | Propyl | Tetrahydrothiopyran-3-yl | 2-$CF_3$ | |
| 2.49 | Ethyl | Tetrahydropyran-3-yl | 3-$CF_3$ | |
| 2.50 | Propyl | Tetrahydropyran-3-yl | 3-$CF_3$ | |
| 2.51 | Ethyl | Tetrahydropyran-4-yl | 3-$CF_3$ | |
| 2.52 | Propyl | Tetrahydropyran-4-yl | 3-$CF_3$ | |
| 2.53 | Ethyl | Tetrahydrothiopyran-3-yl | 3-$CF_3$ | |
| 2.54 | Propyl | Tetrahydrothiopyran-3-yl | 3-$CF_3$ | |
| 2.55 | Ethyl | Tetrahydropyran-3-yl | 4-$CF_3$ | 72–77 |
| 2.56 | Propyl | Tetrahydropyran-3-yl | 4-$CF_3$ | 3,90 (m, 2H), 4,27 (t, 2H), 4,47 (m, 2H) 7,00 (d, 2H), 7,55 (d, 2H) |
| 2.57 | Ethyl | Tetrahydropyran-4-yl | 4-$CF_3$ | |
| 2.58 | Propyl | Tetrahydropyran-4-yl | 4-$CF_3$ | 90–94 |
| 2.59 | Ethyl | Tetrahydrothiopyran-3-yl | 4-$CF_3$ | 73–79 |
| 2.60 | Propyl | Tetrahydrothiopyran-3-yl | 4-$CF_3$ | 4,27 (t, 2H), 4,47 (m, 2H), 7,00 (d, 2H) 7,55 (d, 2H) |
| 2.61 | Ethyl | Tetrahydropyran-3-yl | 2,4-$Cl_2$ | 73–75 |
| 2.62 | Propyl | Tetrahydropyran-3-yl | 2,4-$Cl_2$ | 69–73 |
| 2.63 | Ethyl | Tetrahydropyran-4-yl | 2,4-$Cl_2$ | 4,00 (m, 2H), 4,25 (t, 2H), 4,45 (t, 2H) 6,87 (d, 1H), 7,17 (d, 1H), 7,37 (d, 1H) |
| 2.64 | Propyl | Tetrahydropyran-4-yl | 2,4-$Cl_2$ | 4,00 (m, 2H), 4,25 (t, 2H), 4,45 (t, 2H) 6,87 (d, 1H), 7,17 (d, 1H), 7,37 (d, 1H) |
| 2.65 | Ethyl | Tetrahydrothiopyran-3-yl | 2,4-$Cl_2$ | 4,25 (t, 2H), 4,45 (t, 2H), 6,87 (d, 1H) 7,17 (d, 1H), 7,37 (d, 1H) |
| 2.66 | Propyl | Tetrahydrothiopyran-3-yl | 2,4-$Cl_2$ | 4,25 (t, 2H), 4,45 (t, 2H), 6,87 (d, 1H) 7,17 (d, 1H), 7,37 (d, 1H) |
| 2.67 | Ethyl | Tetrahydropyran-3-yl | 2,4,6-$Cl_3$ | 90–93 |
| 2.68 | Propyl | Tetrahydropyran-3-yl | 2,4,6-$Cl_3$ | 83–87 |
| 2.69 | Ethyl | Tetrahydropyran-4-yl | 2,4,6-$Cl_3$ | 79–82 |
| 2.70 | Propyl | Tetrahydropyran-4-yl | 2,4,6-$Cl_3$ | 4,00 (m, 2H), 4,27 (t, 2H), 4,45 (m, 2H), 7,32 (s, 2H) |
| 2.71 | Ethyl | Tetrahydrothiopyran-3-yl | 2,4,6-$Cl_3$ | 105–108 |
| 2.72 | Propyl | Tetrahydrothiopyran-3-yl | 2,4,6-$Cl_3$ | 4,27 (t, 2H), 4,45 (m, 2H), 7,82 (s, 2H) |
| 2.73 | Ethyl | Tetrahydropyran-3-yl | 4-$NO_2$ | 3,90 (m, 2H), 4,32 (m, 2H), 4,50 (m, 2H), 7,00 (d, 2H), 8,20 (d, 2H) |
| 2.74 | Propyl | Tetrahydropyran-3-yl | 4-$NO_2$ | 3,90 (m, 2H), 4,32 (m, 2H), 4,50 (m, 2H) 7,00 (d, 2H), 8,20 (d, 2H) |
| 2.75 | Ethyl | Tetrahydropyran-4-yl | 4-$NO_2$ | 126–129 |
| 2.76 | Propyl | Tetrahydropyran-4-yl | 4-$NO_2$ | 138–141 |
| 2.77 | Ethyl | Tetrahydrothiopyran-3-yl | 4-$NO_2$ | 4,32 (m, 2H), 4,50 (m, 2H), 7,00 (d, 2H), 8,20 (d, 2H) |
| 2.78 | Propyl | Tetrahydrothiopyran-3-yl | 4-$NO_2$ | 4,32 (m, 2H), 4,50 (m, 2H), 7,00 (d, 2H), 8,20 (d, 2H) |

TABLE 3

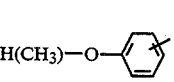

III ($R^e$ = —CH$_2$CH(CH$_3$)—O—⟨Radicals⟩ ; $R^g$, $R^h$, $R^i$ = H)

| No. | $R^d$ | $R^f$ | Radicals on phenyl ring | Phys. data/ $^1$H-NMR [δ in ppm], mp. [°C.] |
|---|---|---|---|---|
| 3.01 | Ethyl | Tetrahydropyran-3-yl | — | |
| 3.02 | Propyl | Tetrahydropyran-3-yl | — | |
| 3.03 | Ethyl | Tetrahydropyran-4-yl | — | |
| 3.04 | Propyl | Tetrahydropyran-4-yl | — | |
| 3.05 | Ethyl | Tetrahydrothiopyran-3-yl | — | |
| 3.06 | Propyl | Tetrahydrothiopyran-3-yl | — | |
| 3.07 | Ethyl | Tetrahydropyran-3-yl | 4-F | |
| 3.08 | Propyl | Tetrahydropyran-3-yl | 4-F | |
| 3.09 | Ethyl | Tetrahydropyran-4-yl | 4-F | |
| 3.10 | Propyl | Tetrahydropyran-4-yl | 4-F | |
| 3.11 | Ethyl | Tetrahydrothiopyran-3-yl | 4-F | |
| 3.12 | Propyl | Tetrahydrothiopyran-3-yl | 4-F | |
| 3.13 | Ethyl | Tetrahydropyran-3-yl | 4-Cl | |
| 3.14 | Propyl | Tetrahydropyran-3-yl | 4-Cl | |
| 3.15 | Ethyl | Tetrahydropyran-4-yl | 4-Cl | 1,35 (m, 3H), 4,05–4,30 (m, 2H), 4,60 (m, 1H), 6,80–7,40 (m, 4H) |
| 3.16 | Propyl | Tetrahydropyran-4-yl | 4-Cl | 1,35 (m, 3H), 4,05–4,30 (m, 2H), 4,60 (m, 1H), 6,80–7,40 (m, 4H) |
| 3.17 | Ethyl | Tetrdhydrothiopyran-3-yl | 4-Cl | 1,35 (m, 3H), 4,05–4,25 (m, 2H), 4,60 (m, 1H), 6,80–7,40 (m, 4H) |
| 3.18 | Propyl | Tetrahydrothiopyran-3-yl | 4-Cl | 1,35 (m, 3H), 4,05–4,30 (m, 2H), 4,60 (m, 1H), 6,80–7,40 (m, 4H) |

TABLE 4

III ($R^e$ = —CH$_2$CH$_2$—S—⟨Radicals⟩ ; $R^g$, $R^h$, $R^i$ = H)

| No. | $R^d$ | $R^f$ | Radicals on phenyl ring | Phys. data/ $^1$H-NMR [δ in ppm], mp. [°C.] |
|---|---|---|---|---|
| 4.01 | Ethyl | Tetrahydropyran-3-yl | — | 3,90 (m, 2H), 4,23 (t, 2H), 7,17–7,43 (m, 5H) |
| 4.02 | Propyl | Tetrahydropyran-3-yl | — | 65 |
| 4.03 | Ethyl | Tetrahydropyran-4-yl | — | 3,97 (m, 2H), 4,23 (t, 2H), 7,17–7,43 (m, 5H) |
| 4.04 | Propyl | Tetrahydropyran-4-yl | — | 3,97 (m, 2H), 4,23 (t, 2H), 7,17–7,43 (m, 5H) |
| 4.05 | Ethyl | Tetrahydrothiopyran-3-yl | — | 4,23 (t, 2H), 7,17–7,43 (m, 5H) |
| 4.06 | Propyl | Tetrahydrothiopyran-3-yl | — | 4,23 (t, 2H), 7,17–7,43 (m, 5H) |
| 4.07 | Ethyl | Tetrahydropyran-3-yl | 4-F | 3,90 (m, 2H), 4,17 (t, 2H), 7,00 (m, 2H), 7,40 (m, 2H) |
| 4.08 | Propyl | Tetrahydropyran-3-yl | 4-F | 3,90 (m, 2H), 4,17 (t, 2H), 7,00 (m, 2H), 7,40 (m, 2H) |
| 4.09 | Ethyl | Tetrahydropyran-4-yl | 4-F | 4,00 (m, 2H), 4,17 (t, 2H), 7,00 (m, 2H), 7,40 (m, 2H) |
| 4.10 | Propyl | Tetrahydropyran-4-yl | 4-F | 4,00 (m, 2H), 4,17 (t, 2H), 7,00 (m, 2H), 7,40 (m, 2H) |
| 4.11 | Ethyl | Tetrahydrothiopyran-3-yl | 4-F | 4,17 (t, 2H), 7,00 (m, 2H), 7,40 (m, 2H), |
| 4.12 | Propyl | Tetrahydrothiopyran-3-yl | 4-F | 4,17 (t, 2H), 7,00 (m, 2H), 7,40 (m, 2H), |
| 4.13 | Ethyl | Tetrahydropyran-3-yl | 4-Cl | 71–75 |
| 4.14 | Propyl | Tetrahydropyran-3-yl | 4-Cl | 63–65 |
| 4.15 | Ethyl | Tetrahydropyran-4-yl | 4-Cl | 4,00 (m, 2H), 4,20 (t, 2H), 7,30 (m, 4H) |
| 4.16 | Propyl | Tetrahydropyran-4-yl | 4-Cl | 4,00 (m, 2H), 4,20 (t, 2H), 7,30 (m, 4H) |
| 4.17 | Ethyl | Tetrahydrothiopyran-3-yl | 4-Cl | 4,20 (t, 2H), 7,30 (m, 4H) |
| 4.18 | Propyl | Tetrahydrothiopyran-3-yl | 4-Cl | 4,20 (t, 2H), 7,30 (m, 4H) |
| 4.19 | Ethyl | Tetrahydropyran-3-yl | 2-Cl | 3,90 (m, 2H), 4,25 (t, 2H), 7,10–7,50 (m, 4H) |
| 4.20 | Propyl | Tetrahydropyran-3-yl | 2-Cl | 3,90 (m, 2H), 4,25 (t, 2H), 7,10–7,50 (m, 4H) |
| 4.21 | Ethyl | Tetrahydropyran-4-yl | 2-Cl | 4,00 (m, 2H), 4,25 (t, 2H), 7,10–7,50 (m, 4H) |
| 4.22 | Propyl | Tetrahydropyran-4-yl | 2-Cl | 4,00 (m, 2H), 4,25 (t, 2H), 7,10–7,50 (m, 4H) |
| 4.23 | Ethyl | Tetrahydrothiopyran-3-yl | 2-Cl | 4,25 (t, 2H) 7,10–7,50 (m, 4H) |
| 4.24 | Propyl | Tetrahydrothiopyran-3-yl | 2-Cl | 4,25 (t, 2H) 7,10–7,50 (m, 4H) |
| 4.25 | Ethyl | Tetrahydropyran-3-yl | 2,6-Cl$_2$ | 3,90 (m, 2H) 4,20 (t, 2H), 7,20 (t, 1H) 7,40 (d, 2H) |
| 4.26 | Propyl | Tetrahydropyran-3-yl | 2,6-Cl$_2$ | 3,90 (m, 2H) 4,20 (t, 2H), 7,20 (t, 1H) 7,40 (d, 2H) |
| 4.27 | Ethyl | Tetrahydropyran-4-yl | 2,6-Cl$_2$ | 61–64 |

TABLE 4-continued

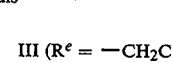

| No. | $R^d$ | $R^f$ | Radicals on phenyl ring | Phys. data/ $^1$H-NMR [δ in ppm], mp. [°C.] |
|---|---|---|---|---|
| 4.28 | Propyl | Tetrahydropyran-4-yl | 2,6-$Cl_2$ | 4,00 (m, 2H) 4,20 (t, 2H), 7,20 (t, 1H) 7,40 (d, 2H) |
| 4.29 | Ethyl | Tetrahydrothiopyran-3-yl | 2,6-$Cl_2$ | 4,20 (t, 2H) 7,20 (t, 2H), 7,40 (d, 2H) |
| 4.30 | Propyl | Tetrahydrothiopyran-3-yl | 2,6-$Cl_2$ | 4,20 (t, 2H) 7,20 (t, 2H), 7,40 (d, 2H) |

TABLE 5

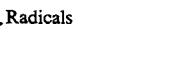

| No. | $R^d$ | $R^f$ | Radicals on phenyl ring | Phys. data/ $^1$H-NMR [δ in ppm], mp. [°C.] |
|---|---|---|---|---|
| 5.01 | Ethyl | Tetrahydropyran-3-yl | — | 3,90 (m, 2H), 4,03 (t, 2H), 4,23 (t,2H), 6,90 (m, 3H), 7,27 (m, 2H) |
| 5.02 | Propyl | Tetrahydropyran-3-yl | — | 3,90 (m, 2H), 4,03 (t, 2H), 4,23 (t, 2H), 6,90 (m, 3H), 7,27 (m, 2H) |
| 5.03 | Ethyl | Tetrahydropyran-4-yl | — | 3,97 (m, 2H), 4,03 (t, 2H), 4,23 (t, 2H), 6,90 (m, 3H), 7,27 (m, 2H) |
| 5.04 | Propyl | Tetrahydropyran-4-yl | — | 3,97 (m, 2H), 4,03 (t, 2H), 4,23 (t, 2H), 6,90 (m, 3H), 7,27 (m, 2H) |
| 5.05 | Ethyl | Tetrahydrothiopyran-3- | — | 4,03 (t, 2H), 4,23 (t, 2H), 6,90 (m, 3H), 7,27 (m, 2H) |
| 5.06 | Propyl | Tetrahydrothiopyran-3- | — | 4,03 (t, 2H), 4,23 (t, 2H), 6,90 (m, 3H), 7,27 (m, 2H) |
| 5.07 | Ethyl | Tetrahydropyran-3-yl | 2-F | 3,90 (m, 2H), 4,10 (t, 2H), 4,27 (t, 2H), 6,80–7,15 (m, 4H) |
| 5.08 | Propyl | Tetrahydropyran-3-yl | 2-F | 3,90 (m, 2H), 4,10 (t, 2H), 4,27 (t, 2H), 6,80–7,15 (m, 4H) |
| 5.09 | Ethyl | Tetrahydropyran-4-yl | 2-F | 4,00 (m, 2H), 4,10 (t, 2H), 4,27 (t, 2H), 6,80–7,15 (m, 4H) |
| 5.10 | Propyl | Tetrahydropyran-4-yl | 2-F | 76–80 |
| 5.11 | Ethyl | Tetrahydrothiopyran-3-yl | 2-F | 4,10 (t, 2H), 4,27 (t, 2H), 6,80–7,15 (m, 4H), |
| 5.12 | Propyl | Tetrahydrothiopyran-3-yl | 2-F | 4,10 (t, 2H), 4,27 (t, 2H), 6,80–7,15 (m, 4H), |
| 5.13 | Ethyl | Tetrahydropyran-3-yl | 3-F | 3,90 (m, 2H), 4,05 (t, 2H), 4,27 (t, 2H), 6,67 (m, 3H), 7,23 (m, 1H) |
| 5.14 | Propyl | Tetrahydropyran-3-yl | 3-F | 3,90 (m, 2H), 4,05 (t, 2H), 4,27 (t, 2H), 6,67 (m, 3H), 7,23 (m, 1H) |
| 5.15 | Ethyl | Tetrahydropyran-4-yl | 3-F | 3,90–4,10 (m, 4H), 4,27 (t, 2H), 6,67 (m, 3H), 7,23 (m, 1H) |
| 5.16 | Propyl | Tetrahydropyran-4-yl | 3-F | 3,90–4,10 (m, 4H), 4,27 (t, 2H), 6,67 (m, 3H), 7,23 (m, 1H) |
| 5.17 | Ethyl | Tetrahydrothiopyran-3-yl | 3-F | 4,05 (t, 2H), 4,27 (t, 2H), 6,67 (m, 3H) 7,23 (m, 1H) |
| 5.18 | Propyl | Tetrahydrothiopyran-3-yl | 3-F | 4,05 (t, 2H), 4,27 (t, 2H), 6,67 (m, 3H) 7,23 (m, 1H) |
| 5.19 | Ethyl | Tetrahydropyran-3-yl | 4-F | 3,90 (m, 2H), 4,03 (t, 2H), 4,27 (t, 2H), 6,90 (m, 2H), 7,00 (m, 2H) |
| 5.20 | Propyl | Tetrahydropyran-3-yl | 4-F | 3,90 (m, 2H), 4,03 (t, 2H), 4,27 (t, 2H), 6,90 (m, 2H), 7,00 (m, 2H) |
| 5.21 | Ethyl | Tetrahydropyran-4-yl | 4-F | 3,90–4,06 (m, 4H), 4,23 (t, 2H), 6,90 (m, 2H), 7,00 (m, 2H) |
| 5.22 | Propyl | Tetrahydropyran-4-yl | 4-F | 3,90–4,06 (m, 4H), 4,28 (t, 2H), 6,90 (m, 2H), 7,00 (m ,2H) |
| 5.23 | Ethyl | Tetrahydrothiopyran-3-yl | 4-F | 4,03 (t, 2H), 4,27 (t, 2H), 6,90 (m, 2H), 7,00 (m, 2H) |
| 5.24 | Propyl | Tetrahydrothiopyran-3-yl | 4-F | 4,03 (t, 2H), 4,27 (t, 2H), 6,90 (m, 2H), 7,00 (m, 2H) |
| 5.25 | Ethyl | Tetrahydropyran-3-yl | 2-Cl | |
| 5.26 | Propyl | Tetrahydropyran-3-yl | 2-Cl | |
| 5.27 | Ethyl | Tetrahydropyran-4-yl | 2-Cl | |
| 5.28 | Propyl | Tetrahydropyran-4-yl | 2-Cl | |
| 5.29 | Ethyl | Tetrahydrothiopyran-3-yl | 2-Cl | |
| 5.30 | Propyl | Tetrahydrothiopyran-3-yl | 2-Cl | |
| 5.31 | Ethyl | Tetrahydropyran-3-yl | 3-Cl | 3,90 (m, 2H), 4,06 (t, 2H), 4,27 (t, 2H), 6,77 (m, 1H), 6,90 (m, 2H), 7,17 (m, 1H) |
| 5.32 | Propyl | Tetrahydropyran-3-yl | 3-Cl | 3,90 (m, 2H), 4,06 (t, 2H), 4,27 (t, 2H), 6,77 (m, 1H), 6,90 (m, 2H), 7,17 (m, 1H) |

TABLE 5-continued

III ($R^e$ = —CH₂CH₂—CH₂—O—Ph-Radicals ; $R^g, R^h, R^i$ = H)

| No. | $R^d$ | $R^f$ | Radicals on phenyl ring | Phys. data/ ¹H-NMR [δ in ppm], mp. [°C.] |
|---|---|---|---|---|
| 5.33 | Ethyl | Tetrahydropyran-4-yl | 3-Cl | 3,90–4,10 (m, 4H), 4,27 (t, 2H), 6,77 (m, 1H), 6,90 (m, 2H), 7,17 (m, 1H) |
| 5.34 | Propyl | Tetrahydropyran-4-yl | 3-Cl | 3,90–4,10 (m, 4H), 4,27 (t, 2H), 6,77 (m, 1H), 6,90 (m, 2H), 7,17 (m, 1H) |
| 5.35 | Ethyl | Tetrahydrothiopyran-3-yl | 3-Cl | 4,06 (t, 2H), 4,27 (t, 2H), 6,77 (m, 1H), 6,90 (m, 2H), 7,17 (m, 1H) |
| 5.36 | Propyl | Tetrahydrothiopyran-3-yl | 3-Cl | 4,06 (t, 2H), 4,27 (t, 2H), 6,77 (m, 1H), 6,90 (m, 2H), 7,17 (m, 1H) |
| 5.37 | Ethyl | Tetrahydropyran-3-yl | 4-Cl | 3,90 (m, 2H), 4,03 (t, 2H), 4,23 (t, 2H), 6,80 (m, 2H), 7,20 (m, 2H) |
| 5.38 | Propyl | Tetrahydropyran-3-yl | 4-Cl | 3,90 (m, 2H), 4,03 (t, 2H), 4,23 (t, 2H), 6,80 (m, 2H), 7,20 (m, 2H) |
| 5.39 | Ethyl | Tetrahydropyran-4-yl | 4-Cl | 3,90–4,09 (m, 4H), 4,23 (t, 2H), 6,80 (m, 2H), 7,20 (m, 2H) |
| 5.40 | Propyl | Tetrahydropyran-4-yl | 4-Cl | 3,90–4,09 (m, 4H), 4,23 (t, 2H), 6,80 (m, 2H), 7,20 (m, 2H) |
| 5.41 | Ethyl | Tetrahydrothiopyran-3-yl | 4-Cl | 4,03 (t, 2H), 4,23 (t, 2H), 6,80 (m, 2H), 7,20 (m, 2H) |
| 5.42 | Propyl | Tetrahydrothiopyran-3-yl | 4-Cl | 4,03 (t, 2H), 4,23 (t, 2H), 6,80 (m, 2H), 7,20 (m, 2H) |
| 5.43 | Ethyl | Tetrahydropyran-3-yl | 4-NO₂ | 3,90 (m, 2H), 4,20 (t, 2H), 4,28 (t, 2H), 6,93 (d, 2H), 8,20 (d, H) |
| 5.44 | Propyl | Tetrahydropyran-3-yl | 4-NO₂ | 3,90 (m, 2H), 4,20 (t, 2H), 4,28 (t, 2H), 6,93 (d, 2H), 8,20 (d, 2H) |
| 5.45 | Ethyl | Tetrahydropyran-4-yl | 4-NO₂ | 4,00 (m, 2H), 4,20 (t, 2H), 4,28 (t, 2H), 6,93 (d, 2H), 8,20 (d, 2H) |
| 5.46 | Propyl | Tetrahydropyran-4-yl | 4-NO₂ | 4,00 (m, 2H), 4,20 (t, 2H), 4,28 (t, 2H), 6,93 (d, 2H), 8,20 (d, 2H) |
| 5.47 | Ethyl | Tetrahydrothiopyran-3-yl | 4-NO₂ | 4,20 (t, 2H), 4,28 (t, 2H), 6,93 (d, 2H), 8,20 (d, 2H) |
| 5.48 | Propyl | Tetrahydrothiopyran-3-yl | 4-NO₂ | 4,20 (t, 2H), 4,28 (t, 2H), 6,93 (d, 2H), 8,20 (d, 2H) |
| 5.49 | Ethyl | Tetrahydropyran-3-yl | 4-Br | 3,90 (m, 2H), 4,00 (t, 2H), 4,27 (t, 2H), 6,80 (d, 2H), 7,37 (d, 2H) |
| 5.50 | Propyl | Tetrahydropyran-3-yl | 4-Br | 3,90 (m, 2H), 4,00 (t, 2H), 4,27 (t, 2H), 6,80 (d, 2H), 7,37 (d, 2H) |
| 5.51 | Ethyl | Tetrahydropyran-4-yl | 4-Br | 3,90–4,10 (m, 4H), 4,27 (t, 2H), 6,80 (d, 2H), 7,37 (d, 2H) |
| 5.52 | Propyl | Tetrahydropyran-4-yl | 4-Br | 3,90–4,10 (m, 4H), 4,27 (t, 2H), 6,80 (d, 2H), 7,37 (d, 2H) |
| 5.53 | Ethyl | Tetrahydrothiopyran-4-yl | 4-Br | 4,00 (t, 2H), 4,27 (t, 2H), 6,80 (d, 2H), 7,37 (d, 2H) |
| 5.54 | Propyl | Tetrahydrothiopyran-4-yl | 4-Br | 4,00 (t, 2H), 4,27 (t, 2H), 6,80 (d, 2H), 7,37 (d, 2H) |

TABLE 6

III ($R^e$ = —CH₂CH₂CH₂—S—Ph-Radicals ; $R^g, R^h, R^i$ = H)

| No. | $R^d$ | $R^f$ | Radicals on phenyl ring | Phys. data/ ¹H-NMR [δ in ppm], mp. [°C.] |
|---|---|---|---|---|
| 6.01 | Ethyl | Tetrahydropyran-3-yl | — | 3,90 (m, 2H), 4,17 (t, 2H), 7,10–7,40 (m, 5H) |
| 6.02 | Propyl | Tetrahydropyran-3-yl | — | 3,90 (m, 2H), 4,17 (t, 2H), 7,10–7,40 (m, 5H) |
| 6.03 | Ethyl | Tetrahydropyran-4-yl | — | 4,00 (m, 2H), 4,17 (t, 2H), 7,10–7,40 (m, 5H) |
| 6.04 | Propyl | Tetrahydropyran-4-yl | — | 4,00 (m, 2H), 4,17 (t, 2H), 7,10–7,40 (m, 5H) |
| 6.05 | Ethyl | Tetrahydrothiopyran-3-yl | — | 4,17 (t, 2H), 7,10–7,40 (m, 5H) |
| 6.06 | Propyl | Tetrahydrothiopyran-3-yl | — | 4,17 (t, 2H), 7,10–7,40 (m, 5H) |
| 6.07 | Ethyl | Tetrahydropyran-3-yl | 4-F | 3,90 (m, 2H), 4,17 (t, 2H), 7,00 (t, 2H), 7,33 (m, 2H) |
| 6.08 | Propyl | Tetrahydropyran-3-yl | 4-F | 3,90 (m, 2H), 4,17 (t, 2H), 7,00 (t, 2H), 7,33 (m, 2H) |
| 6.09 | Ethyl | Tetrahydropyran-4-yl | 4-F | 4,00 (m, 2H), 4,17 (t, 2H), 7,00 (t, 2H), 7,33 (m, 2H) |
| 6.10 | Propyl | Tetrahydropyran-4-yl | 4-F | 4,00 (m, 2H), 4,17 (t, 2H), 7,00 (t, 2H), 7,33 (m, 2H) |
| 6.11 | Ethyl | Tetrahydrothiopyran-3-yl | 4-F | 4,17 (t, 2H), 7,00 (t, 2H), 7,33 (m, 2H) |

TABLE 6-continued

III ($R^e$ = —CH₂CH₂CH₂—S—⟨phenyl⟩-Radicals ; $R^g$, $R^h$, $R^i$ = H)

| No. | $R^d$ | $R^f$ | Radicals on phenyl ring | Phys. data/ ¹H-NMR [δ in ppm], mp. [°C.] |
|---|---|---|---|---|
| 6.12 | Propyl | Tetrahydrothiopyran-3-yl | 4-F | 4,17 (t, 2H), 7,00 (t, 2H), 7,33 (m, 2H) |
| 6.13 | Ethyl | Tetrahydropyran-3-yl | 4-Cl | 3,90 (m, 2H), 4,17 (t, 2H), 7,27 (s, 4H) |
| 6.14 | Propyl | Tetrahydropyran-3-yl | 4-Cl | 3,90 (m, 2H), 4,17 (t, 2H), 7,27 (s, 4H) |
| 6.15 | Ethyl | Tetrahydropyran-4-yl | 4-Cl | 4,00 (m, 2H), 4,17 (t, 2H), 7,27 (s, 4H) |
| 6.16 | Propyl | Tetrahydropyran-4-yl | 4-Cl | 4,00 (m, 2H), 4,17 (t, 2H), 7,27 (s, 4H) |
| 6.17 | Ethyl | Tetrahydrothiopyran-3-yl | 4-Cl | 4,17 (t, 2H), 7,27 (s, 4H) |
| 6.18 | Propyl | Tetrahydrothiopyran-3-yl | 4-Cl | 4,17 (t, 2H), 7,27 (s, 4H) |
| 6.19 | Ethyl | Tetrahydropyran-3-yl | 2-Cl | 3,90 (m, 2H), 4,20 (t, 2H), 7,07–7,40 (m, 4H) |
| 6.20 | Propyl | Tetrahydropyran-3-yl | 2-Cl | 3,90 (m, 2H), 4,20 (t, 2H), 7,07–7,40 (m, 4H) |
| 6.21 | Ethyl | Tetrahydropyran-4-yl | 2-Cl | 4,00 (m, 2H), 4,20 (t, 2H), 7,07–7,40 (m, 4H) |
| 6.22 | Propyl | Tetrahydropyran-4-yl | 2-Cl | 4,00 (m, 2H), 4,20 (t, 2H), 7,07–7,40 (m, 4H) |
| 6.23 | Ethyl | Tetrahydrothiopyran-3-yl | 2-Cl | 4,20 (t, 2H), 7,07–7,40 (m, 4H) |
| 6.24 | Propyl | Tetrahydrothiopyran-3-yl | 2-Cl | 4,20 (t, 2H), 7,07–7,40 (m, 4H) |
| 6.25 | Ethyl | Tetrahydropyran-3-yl | 3-Cl | 3,90 (m, 2H), 4,20 (t, 2H), 7,17 (m, 3H) 7,30 (m, 1H) |
| 6.26 | Propyl | Tetrahydropyrdn-3-yl | 3-Cl | 3,90 (m, 2H), 4,20 (t, 2H), 7,17 (m, 3H) 7,30 (m, 1H) |
| 6.27 | Ethyl | Tetrahydropyran-4-yl | 3-Cl | 4,00 (m, 2H), 4,20 (t, 2H), 7,17 (m, 3H) 7,30 (m, 1H) |
| 6.28 | Propyl | Tetrahydropyran-4-yl | 3-Cl | 4,00 (m, 2H), 4,20 (t, 2H), 7,17 (m, 3H) 7,30 (m, 1H) |
| 6.29 | Ethyl | Tetrahydrothiopyran-3-yl | 3-Cl | 4,20 (t, 2H), 7,17 (m, 3H), 7,30 (m, 1H) |
| 6.30 | Propyl | Tetrahydrothiopyran-3-yl | 3-Cl | 4,20 (t, 2H), 7,17 (m, 3H), 7,30 (m, 1H) |
| 6.31 | Ethyl | Tetrahydropyran-3-yl | 2,5-Cl₂ | 3,90 (m, 2H), 4,20 (t, 2H), 7,07 (dd, 1H), 7,20 (d, 1H), 7,30 (d, 1H) |
| 6.32 | Propyl | Tetrahydropyran-3-yl | 2,5-Cl₂ | 3,90 (m, 2H), 4,20 (t, 2H), 7,07 (dd, 1H), 7,20 (d, 1H), 7,30 (d, 1H) |
| 6.33 | Ethyl | Tetrahydropyran-4-yl | 2,5-Cl₂ | 4,00 (m, 2H), 4,20 (t, 2H), 7,07 (dd, 1H), 7,20 (d, 1H), 7,30 (d, 1H) |
| 6.34 | Propyl | Tetrahydropyran-4-yl | 2,5-Cl₂ | 4,00 (m, 2H), 4,20 (t, 2H), 7,07 (dd, 1H), 7,20 (d, 1H), 7,30 (d, 1H) |
| 6.35 | Ethyl | Tetrahydrothiopyran-3-yl | 2,5-Cl₂ | 4,20 (t, 2H), 7,07 (dd, 1H), 7,20 (d, 1H) 7,30 (d, 1H) |
| 6.36 | Propyl | Tetrahydrothiopyran-3-yl | 2,5-Cl₂ | 4,20 (t, 2H), 7,07 (dd, 1H), 7,20 (d, 1H) 7,30 (d, 1H) |
| 6.37 | Ethyl | Tetrahydropyran-3-yl | 2,6-Cl₂ | 3,90 (m, 2H), 4,20 (t, 2H), 7,20 (t, 1H) 7,40 (d, 2H) |
| 6.38 | Propyl | Tetrahydropyran-3-yl | 2,6-Cl₂ | 3,90 (m, 2H), 4,20 (t, 2H), 7,20 (t, 1H) 7,40 (d, 2H) |
| 6.39 | Ethyl | Tetrahydropyran-4-yl | 2,6-Cl₂ | 4,00 (m, 2H), 4,20 (t, 2H), 7,20 (t, 1H) 7,40 (d, 2H) |
| 6.40 | Propyl | Tetrahydropyran-4-yl | 2,6-Cl₂ | 4,00 (m, 2H), 4,20 (t, 2H), 7,20 (t, 1H) 7,40 (d, 2H) |
| 6.41 | Ethyl | Tetrahydrothiopyran-3-yl | 2,6-Cl₂ | 4,20 (t, 2H), 7,20 (t, 1H), 7,40 (d, 2H) |
| 6.42 | Propyl | Tetrahydrothiopyran-3-yl | 2,6-Cl₂ | 4,20 (t, 2H), 7,20 (t, 1H), 7,40 (d, 2H) |

TABLE 7

III ($R^e$ = —CH₂CH₂—O—CH₂—⟨phenyl⟩-Radicals ; $R^g$, $R^h$, $R^i$ = H)

| No. | $R^d$ | $R^f$ | Radicals on phenyl ring | Phys. data/ ¹H-NMR [δ in ppm], mp. [°C.] |
|---|---|---|---|---|
| 7.01 | Ethyl | Tetrahydropyran-3-yl | — | 3,90 (m, 2H), 4,25 (t, 2H), 4,58 (s, 2H), 7,38 (s, 5H) |
| 7.02 | Propyl | Tetrahydropyran-3-yl | — | 3,90 (m, 2H), 4,25 (t, 2H), 4,58 (s, 2H), 7,38 (s, 5H) |
| 7.03 | Ethyl | Tetrahydropyran-4-yl | — | 4,03 (m, 2H), 4,33 (m, 2H), 4,60 (s, 2H), 7,40 (s, 5H) |
| 7.04 | Propyl | Tetrahydropyran-4-yl | — | 4,03 (m, 2H), 4,33 (m, 2H), 4,60 (s, 2H), 7,40 (s, 5H) |
| 7.05 | Ethyl | Tetrahydrothiopyran-3-yl | — | 4,27 (m, 2H), 4,57 (s, 2H), 7,35 (s, 5H) |
| 7.06 | Propyl | Tetrahydrothiopyran-3-yl | — | 4,27 (m, 2H), 4,57 (s, 2H), 7,35 (s, 5H) |
| 7.07 | Ethyl | Tetrahydropyran-3-yl | 2-F | 3,93 (m, 2H), 4,27 (m, 2H), 4,67 (s, 2H), 6,93–7,50 (m, 4H) |
| 7.08 | Propyl | Tetrahydropyran-3-yl | 2-F | 3,93 (m, 2H), 4,27 (m, 2H), 4,67 (s, 2H), 6,93–7,50 (m, 4H) |

TABLE 7-continued

| No. | $R^d$ | $R^f$ | Radicals on phenyl ring | Phys. data/ $^1$H-NMR [δ in ppm], mp. [°C.] |
|---|---|---|---|---|
| 7.09 | Ethyl | Tetrahydropyran-4-yl | 2-F | 4,03 (m, 2H), 4,27 (m, 2H), 4,63 (s, 2H), 6,97–7,50 (m, 4H) |
| 7.10 | Propyl | Tetrahydropyran-4-yl | 2-F | 4,03 (m, 2H), 4,27 (m, 2H), 4,63 (s, 2H), 6,97–7,50 (m, 4H) |
| 7.11 | Ethyl | Tetrahydrothiopyran-3-yl | 2-F | 4,27 (m, 2H), 4,67 (s, 2H), 6,97–7,50 (m, 4H) |
| 7.12 | Propyl | Tetrahydrothiopyran-3-yl | 2-F | 4,27 (m, 2H), 4,67 (s, 2H), 6,97–7,50 (m, 4H) |
| 7.13 | Ethyl | Tetrahydropyran-3-yl | 3-F | 3,93 (m, 2H), 4,27 (m, 2H), 4,57 (s, 2H), 6,90–7,15 (m, 3H), 7,23–7,40 (m, 1H) |
| 7.14 | Propyl | Tetrahydropyran-3-yl | 3-F | 3,93 (m, 2H), 4,27 (m, 2H), 4,57 (s, 2H), 6,90–7,15 (m, 3H), 7,23–7,40 (m, 1H) |
| 7.15 | Ethyl | Tetrahydropyran-4-yl | 3-F | 4,03 (m, 2H), 4,25 (m, 2H), 4,60 (s, 2H), 6,90–7,18 (m, 3H), 7,26–7,40 (m, 1H) |
| 7.16 | Propyl | Tetrahydropyran-4-yl | 3-F | 4,03 (m, 2H), 4,25 (m, 2H), 4,60 (s, 2H), 6,90–7,18 (m, 3H), 7,26–7,40 (m, 1H) |
| 7.17 | Ethyl | Tetrahydrothiopyran-3-yl | 3-F | 4,27 (m, 2H), 4,60 (s, 2H), 6,90–7,15 (m, 3H), 7,23–7,40 (m, 1H) |
| 7.18 | Propyl | Tetrahydrothiopyran-3-yl | 3-F | 4,27 (m, 2H), 4,60 (s, 2H), 6,90–7,15 (m, 3H), 7,23–7,40 (m, 1H) |
| 7.19 | Ethyl | Tetrahydropyran-3-yl | 4-F | 3,93 (m, 2H), 4,23 (m, 2H), 4,53 (s, 2H), 7,00 (m, 2H), 7,30 (m, 2H) |
| 7.20 | Propyl | Tetrahydropyran-3-yl | 4-F | 3,93 (m, 2H), 4,23 (m, 2H), 4,53 (s, 2H), 7,00 (m, 2H), 7,30 (m, 2H) |
| 7.21 | Ethyl | Tetrahydropyran-4-yl | 4-F | 92 |
| 7.22 | Propyl | Tetrahydropyran-4-yl | 4-F | 4,00 (m, 2H), 4,23 (m, 2H), 4,53 (s, 2H), 7,03 (m, 2H), 7,30 (m, 2H) |
| 7.23 | Ethyl | Tetrahydrothiopyran-3-yl | 4-F | 4,27 (m, 2H), 4,53 (s, 2H), 7,03 (m, 2H), 7,30 (m, 2H) |
| 7.24 | Propyl | Tetrahydrothiopyran-3-yl | 4-F | 4,27 (m, 2H), 4,53 (s, 2H), 7,03 (m, 2H), 7,30 (m, 2H) |
| 7.25 | Ethyl | Tetrahydropyran-3-yl | 2-Cl | |
| 7.26 | Propyl | Tetrahydropyran-3-yl | 2-Cl | |
| 7.27 | Ethyl | Tetrahydropyran-4-yl | 2-Cl | |
| 7.28 | Propyl | Tetrahydropyran-4-yl | 2-Cl | |
| 7.29 | Ethyl | Tetrahydrothiopyran-3-yl | 2-Cl | |
| 7.30 | Propyl | Tetrahydrothiopyran-3-yl | 2-Cl | |
| 7.31 | Ethyl | Tetrahydropyran-3-yl | 3-Cl | |
| 7.32 | Propyl | Tetrahydropyran-3-yl | 3-Cl | |
| 7.33 | Ethyl | Tetrahydropyran-4-yl | 3-Cl | |
| 7.34 | Propyl | Tetrahydropyran-4-yl | 3-Cl | |
| 7.35 | Ethyl | Tetrahydrothiopyran-3-yl | 3-Cl | |
| 7.36 | Propyl | Tetrahydrothiopyran-3-yl | 3-Cl | |
| 7.37 | Ethyl | Tetrahydropyran-3-yl | 4-Cl | 3,93 (m, 2H), 4,27 (m, 2H), 4,53 (s, 2H), 7,28 (m, 4H) |
| 7.38 | Propyl | Tetrahydropyran-3-yl | 4-Cl | 3,93 (m, 2H), 4,27 (m, 2H), 4,53 (s, 2H), 7,28 (m, 4H) |
| 7.39 | Ethyl | Tetrahydropyran-4-yl | 4-Cl | 67–72 |
| 7.40 | Propyl | Tetrahydropyran-4-yl | 4-Cl | 4,00 (m, 2H), 4,23 (m, 2H), 4,53 (s, 2H), 7,28 (m, 4H) |
| 7.41 | Ethyl | Tetrahydrothiopyran-3-yl | 4-Cl | 4,27 (m, 2H), 4,53 (s, 2H), 7,28 (m, 4H) |
| 7.42 | Propyl | Tetrahydrothiopyran-3-yl | 4-Cl | 4,27 (m, 2H), 4,53 (s, 2H), 7,28 (m, 4H) |
| 7.43 | Ethyl | Tetrahydropyran-3-yl | 2-$CH_3$ | 3,93 (m, 2H), 4,23 (m, 2H), 4,57 (s, 2H), 7,09–7,33 (m, 4H) |
| 7.44 | Propyl | Tetrahydropyran-3-yl | 2-$CH_3$ | 3,93 (m, 2H), 4,23 (m, 2H), 4,57 (s, 2H), 7,09–7,33 (m, 4H) |
| 7.45 | Ethyl | Tetrahydropyran-4-yl | 2-$CH_3$ | 4,00 (m, 2H), 4,23 (m, 2H), 4,57 (s, 2H), 7,09–7,33 (m, 4H) |
| 7.46 | Propyl | Tetrahydropyran-4-yl | 2-$CH_3$ | 4,00 (m, 2H), 4,23 (m, 2H), 4,57 (s, 2H), 7,09–7,33 (m, 4H) |
| 7.47 | Ethyl | Tetrahydrothiopyran-3-yl | 2-$CH_3$ | 4,23 (m, 2H), 4,57 (s, 2H), 7,09–7,33 (m, 4H) |
| 7.48 | Propyl | Tetrahydrothiopyran-3-yl | 2-$CH_3$ | 4,23 (m, 2H), 4,57 (s, 2H), 7,09–7,33 (m, 4H) |
| 7.49 | Ethyl | Tetrahydropyran-3-yl | 3-$CH_3$ | 3,93 (m, 2H), 4,25 (m, 2H), 4,57 (s, 2H), 7,00–7,32 (m, 4H) |
| 7.50 | Propyl | Tetrahydropyran-3-yl | 3-$CH_3$ | 3,93 (m, 2H), 4,25 (m, 2H), 4,57 (s, 2H), 7,00–7,32 (m, 4H) |
| 7.51 | Ethyl | Tetrahydropyrdn-4-yl | 3-$CH_3$ | 4,00 (m, 2H), 4,27 (m, 2H), 4,57 (s, 2H), 7,00–7,32 (m, 4H) |
| 7.52 | Propyl | Tetrahydropyran-4-yl | 3-$CH_3$ | 4,00 (m, 2H), 4,27 (m, 2H), 4,57 (s, 2H), 7,00–7,32 (m, 4H) |
| 7.53 | Ethyl | Tetrdhydrothiopyran-3-yl | 3-$CH_3$ | 4,27 (m, 2H), 4,60 (s, 2H), |

TABLE 7-continued

III ($R^e$ = —CH$_2$CH$_2$—O—CH$_2$—Ar-Radicals ; $R^g$, $R^h$, $R^i$ = H)

| No. | $R^d$ | $R^f$ | Radicals on phenyl ring | Phys. data/ $^1$H-NMR [δ in ppm], mp. [°C.] |
|---|---|---|---|---|
| 7.54 | Propyl | Tetrahydrothiopyran-3-yl | 3-CH$_3$ | 7,00–7,32 (m, 4H) 4,27 (m, 2H), 4,60 (s, 2H), 7,00–7,32 (m, 4H) |
| 7.55 | Ethyl | Tetrahydropyran-3-yl | 4-CH$_3$ | 3,93 (m, 2H), 4,20 (m, 2H), 4,53 (s, 2H), 7,07–7,30 (m, 4H) |
| 7.56 | Propyl | Tetrahydropyran-3-yl | 4-CH$_3$ | 3,93 (m, 2H), 4,20 (m, 2H), 4,53 (s, 2H), 7,07–7,30 (m, 4H) |
| 7.57 | Ethyl | Tetrahydropyran-4-yl | 4-CH$_3$ | 4,00 (m, 2H), 4,23 (m, 2H), 4,57 (s, 2H), 7,03–7,27 (m, 4H) |
| 7.58 | Propyl | Tetrahydropyran-4-yl | 4-CH$_3$ | 4,00 (m, 2H), 4,23 (m, 2H), 4,57 (s, 2H), 7,03–7,27 (m, 4H) |
| 7.59 | Ethyl | Tetrahydrothiopyran-3-yl | 4-CH$_3$ | 4,23 (m, 2H), 4,57 (s, 2H), 7,07–7,30 (m, 4H) |
| 7.60 | Propyl | Tetrahydrothiopyran-3-yl | 4-CH$_3$ | 4,28 (m, 2H), 4,57 (s, 2H), 7,07–7,30 (m, 4H) |
| 7.61 | Ethyl | Tetrahydropyran-3-yl | 4-tert.-C$_4$H$_9$ | 3,93 (m, 2H), 4,23 (m, 2H), 4,53 (s, 2H), 7,20–7,40 (m, 4H) |
| 7.62 | Propyl | Tetrahydropyran-3-yl | 4-tert.-C$_4$H$_9$ | 3,93 (m, 2H), 4,23 (m, 2H), 4,53 (s, 2H), 7,20–7,40 (m, 4H) |
| 7.63 | Ethyl | Tetrahydropyran-4-yl | 4-tert.-C$_4$H$_9$ | 4,00 (m, 2H), 4,23 (m, 2H), 4,53 (s, 2H), 7,20–7,40 (m, 4H) |
| 7.64 | Propyl | Tetrahydropyran-4-yl | 4-tert.-C$_4$H$_9$ | 4,00 (m, 2H), 4,23 (m, 2H), 4,53 (s, 2H), 7,20–7,40 (m, 4H) |
| 7.65 | Ethyl | Tetrahydrothiopyran-3-yl | 4-tert.-C$_4$H$_9$ | 4,23 (m, 2H), 4,53 (s, 2H), 7,20–7,40 (m, 4H) |
| 7.66 | Propyl | Tetrahydrothiopyran-3-yl | 4-tert.-C$_4$H$_9$ | 4,23 (m, 2H), 4,53 (s, 2H), 7,20–7,40 (m, 4H) |

TABLE 8

III ($R^e$ = —CH$_2$CH$_2$—S—CH$_2$—Ar-Radicals ; $R^g$, $R^h$, $R^i$ = H)

| No. | $R^d$ | $R^f$ | Radicals on phenyl ring | Phys. data/$^1$H-NMR [δ in ppm], mp. [°C.] |
|---|---|---|---|---|
| 8.01 | Ethyl | Tetrahydropyran-3-yl | — | 3,73 (s, 2H), 3,90 (m, 2H), 4,17 (t, 2H), 7,28 (s, 5H) |
| 8.02 | Propyl | Tetrahydropyran-3-yl | — | 3,73 (s, 2H), 3,90 (m, 2H), 4,17 (t, 2H), 7,28 (s, 5H) |
| 8.03 | Ethyl | Tetrahydropyran-4-yl | — | 3,77 (s, 2H), 4,00 (m, 2H), 4,13 (t, 2H), 7,28 (s, 5H) |
| 8.04 | Propyl | Tetrahydropyran-4-yl | — | 3,77 (s, 2H), 4,00 (m, 2H), 4,13 (t, 2H), 7,28 (s, 5H) |
| 8.05 | Ethyl | Tetrahydrothiopyran-3-yl | — | 3,80 (s, 2H), 4,13 (t, 2H), 7,28 (s, 5H) |
| 8.06 | Propyl | Tetrahydrothiopyran-3-yl | — | 3,80 (s, 2H), 4,13 (t, 2H), 7,28 (s, 5H) |
| 8.07 | Ethyl | Tetrahydropyran-3-yl | 4-F | 3,72 (s, 2H), 3,90 (m, 2H), 4,13 (t, 2H), 7,00 (m, 2H), 7,30 (m, 2H) |
| 8.08 | Propyl | Tetrahydropyran-3-yl | 4-F | 3,72 (s, 2H), 3,90 (m, 2H), 4,13 (t, 2H), 7,00 (m, 2H), 7,30 (m, 2H) |
| 8.09 | Ethyl | Tetrahydropyran-4-yl | 4-F | 63–65 |
| 8.10 | Propyl | Tetrahydropyran-4-yl | 4-F | 3,73 (s, 2H), 4,00 (m, 2H), 4,13 (t, 2H), 7,00 (m, 2H), 7,30 (m, 2H) |
| 8.11 | Ethyl | Tetrahydrothiopyran-3-yl | 4-F | 3,75 (s, 2H), 4,13 (t, 2H), 7,00 (m, 2H), 7,30 (m, 2H) |
| 8.12 | Propyl | Tetrahydrothiopyran-3-yl | 4-F | 3,75 (s, 2H), 4,13 (t, 2H), 7,00 (m, 2H), 7,30 (m, 2H) |
| 8.13 | Ethyl | Tetrahydropyran-3-yl | 4-Cl | 3,77 (s, 2H), 3,93 (m, 2H), 4,13 (t, 2H), 7,30 (s, 4H) |
| 8.14 | Propyl | Tetrahydropyran-3-yl | 4-Cl | 3,77 (s, 2H), 3,93 (m, 2H), 4,13 (t, 2H), 7,30 (s, 4H) |
| 8.15 | Ethyl | Tetrahydropyran-4-yl | 4-Cl | 3,73 (s, 2H), 4,00 (m, 2H), 4,17 (t, 2H), 7,30 (s, 4H) |
| 8.16 | Propyl | Tetrahydropyran-4-yl | 4-Cl | 3,73 (s, 2H), 4,00 (m, 2H), 4,17 (t, 2H), 7,30 (s, 4H) |
| 8.17 | Ethyl | Tetrahydrothiopyran-3-yl | 4-Cl | 3,73 (s, 2H), 4,13 (m, 2H), 7,30 (s, 4H) |

TABLE 8-continued

III ($R^e$ = —CH₂CH₂—S—CH₂—phenyl-Radicals ; $R^g$, $R^h$, $R^i$ = H)

| No. | $R^d$ | $R^f$ | Radicals on phenyl ring | Phys. data/¹H-NMR [δ in ppm], mp. [°C.] |
|---|---|---|---|---|
| 8.18 | Propyl | Tetrahydrothiopyran-3-yl | 4-Cl | 3,73 (s, 2H), 4,13 (m, 2H), 7,30 (s, 4H) |

TABLE 9

III ($R^e$ = —CH₂CH₂CH₂CH₂—O—phenyl-Radicals ; $R^g$, $R^h$, $R^i$ = H)

| No. | $R^d$ | $R^f$ | Radicals on phenyl ring | Phys. data/¹H-NMR [δ in ppm], mp. [°C.] |
|---|---|---|---|---|
| 9.01 | Ethyl | Tetrahydropyran-3-yl | — | 3,70–4,20 (m, 6H), 6,90 (m, 3H), 7,30 (m, 2H) |
| 9.02 | Propyl | Tetrahydropyran-3-yl | — | 3,70–4,20 (m, 6H), 6,90 (m, 3H), 7,30 (m, 2H) |
| 9.03 | Ethyl | Tetrahydropyran-4-yl | — | 3,83–4,23 (m, 6H), 6,90 (m, 3H), 7,30 (m, 2H) |
| 9.04 | Propyl | Tetrahydropyran-4-yl | — | 3,83–4,23 (m, 6H), 6,90 (m, 3H), 7,30 (m, 2H) |
| 9.05 | Ethyl | Tetrahydrothiopyran-3-yl | — | 4,00 (bs, 2H), 4,13 (bs, 2H), 6,90 (m, 3H) 7,30 (m, 2H) |
| 9.06 | Propyl | Tetrahydrothiopyran-3-yl | — | 4,00 (bs, 2H), 4,13 (bs, 2H), 6,90 (m, 3H) 7,30 (m, 2H) |
| 9.07 | Ethyl | Tetrahydropyran-3-yl | 2-F | 3,93 (m, 2H), 4,00–4,20 (m, 4H), 6,80–7,15 (m, 4H) |
| 9.08 | Propyl | Tetrahydropyran-3-yl | 2-F | 3,93 (m, 2H), 4,00–4,20 (m, 4H), 6,80–7,15 (m, 4H) |
| 9.09 | Ethyl | Tetrahydropyran-4-yl | 2-F | 68–72 |
| 9.10 | Propyl | Tetrahydropyran-4-yl | 2-F | 3,90–4,20 (m, 6H), 6,80–7,15 (m, 4H) |
| 9.11 | Ethyl | Tetrahydrothiopyran-3-yl | 2-F | 4,00–4,20 (m, 4H), 6,80–7,15 (m, 4H) |
| 9.12 | Propyl | Tetrahydrothiopyran-3-yl | 2-F | 4,00–4,20 (m, 4H), 6,80–7,15 (m, 4H) |
| 9.13 | Ethyl | Tetrahydropyran-3-yl | 3-F | |
| 9.14 | Propyl | Tetrahydropyran-3-yl | 3-F | |
| 9.15 | Ethyl | Tetrahydropyran-4-yl | 3-F | |
| 9.16 | Propyl | Tetrahydropyran-4-yl | 3-F | |
| 9.17 | Ethyl | Tetrahydrothiopyran-3-yl | 3-F | |
| 9.18 | Propyl | Tetrahydrothiopyran-3-yl | 3-F | |
| 9.19 | Ethyl | Tetrahydropyran-3-yl | 4-F | 3,80–4,20 (m, 6H), 6,75–7,05 (m, 4H) |
| 9.20 | Propyl | Tetrahydropyran-3-yl | 4-F | 3,80–4,20 (m, 6H), 6,75–7,05 (m, 4H) |
| 9.21 | Ethyl | Tetrahydropyran-4-yl | 4-F | 3,90–4,20 (m, 6H), 6,75–7,05 (m, 4H) |
| 9.22 | Propyl | Tetrahydropyran-4-yl | 4-F | 3,90–4,20 (m, 6H), 6,75–7,05 (m, 4H) |
| 9.23 | Ethyl | Tetrahydrothiopyran-3-yl | 4-F | 3,90–4,20 (m, 4H), 6,75–7,05 (m, 4H) |
| 9.24 | Propyl | Tetrahydrothiopyran-3-yl | 4-F | 3,90–4,20 (m, 4H), 6,75–7,05 (m, 4H) |
| 9.25 | Ethyl | Tetrahydropyran-3-yl | 4-Cl | 3,80–4,20 (m, 6H), 6,80 (m, 2H), 7,20 (m, 2H) |
| 9.26 | Propyl | Tetrahydropyran-3-yl | 4-Cl | 3,80–4,20 (m, 6H), 6,80 (m, 2H), 7,20 (m, 2H) |
| 9.27 | Ethyl | Tetrahydropyran-4-yl | 4-Cl | 3,90–4,20 (m, 6H), 6,80 (m, 2H), 7,20 (m, 2H) |
| 9.28 | Propyl | Tetrahydropyran-4-yl | 4-Cl | 3,90–4,20 (m, 6H), 6,80 (m, 2H), 7,20 (m, 2H) |
| 9.29 | Ethyl | Tetrahydrothiopyran-3-yl | 4-Cl | 3,90–4,20 (m, 4H), 6,80 (m, 2H), 7,20 (m, 2H) |
| 9.30 | Propyl | Tetrahydrothiopyran-3-yl | 4-Cl | 3,90–4,20 (m, 4H), 6,80 (m, 2H), 7,20 (m, 2H) |
| 9.31 | Ethyl | Tetrahydropyran-3-yl | 2,6-Cl₂ | 3,93 (m, 2H), 4,00–4,25 (m, 4H), 7,00 (t, 1H), 7,30 (d, 2H) |
| 9.32 | Propl | Tetrahydropyran-3-yl | 2,6-Cl₂ | 3,93 (m, 2H), 4,00–4,25 (m, 4H), 7,00 (t, 1H), 7,30 (d, 2H) |
| 9.33 | Ethyl | Tetrahydropyran-4-yl | 2,6-Cl₂ | 3,90–4,25 (m, 6H), 7,00 (t, 1H), 7,30 (d, 2H) |
| 9.34 | Propyl | Tetrahydropyran-4-yl | 2,6-Cl₂ | 3,90–4,25 (m, 6H), 7,00 (t, 1H), 7,30 (d, 2H) |
| 9.35 | Ethyl | Tetrahydrothiopyran-3-yl | 2,6-Cl₂ | 4,00–4,20 (m, 4H), 7,00 (t, 1H), 7,30 (d, 2H) |
| 9.36 | Propyl | Tetrahydrothiopyran-3-yl | 2,6-Cl₂ | 4,00–4,20 (m, 4H), 7,00 (t, 1H), |

TABLE 9-continued

III ($R^e$ = —CH₂CH₂CH₂CH₂—O—[phenyl]—Radicals ; $R^g$, $R^h$, $R^i$ = H)

| No. | $R^d$ | $R^f$ | Radicals on phenyl ring | Phys. data/¹H-NMR [δ in ppm], mp. [°C.] |
|---|---|---|---|---|
| | | | | 7,30 (d, 2H) |

TABLE 10

III ($R^e$ = —CH₂CH₂—O—CH₂CH₂—[phenyl]—Radicals ; $R^g$, $R^h$, $R^i$ = H)

| No. | $R^d$ | $R^f$ | Radicals on phenyl ring | Phys. data/¹H-NMR [δ in ppm], mp. [°C.] |
|---|---|---|---|---|
| 10.01 | Ethyl | Tetrahydropyran-3-yl | — | 3,90 (m, 2H), 4,20 (m, 2H), 7,25 (m, 5H) |
| 10.02 | Propyl | Tetrahydropyran-3-yl | — | 3,90 (m, 2H), 4,20 (m, 2H), 7,25 (m, 5H) |
| 10.03 | Ethyl | Tetrahydropyran-4-yl | — | |
| 10.04 | Propyl | Tetrahydropyran-4-yl | — | |
| 10.05 | Ethyl | Tetrahydrothiopyran-3-yl | — | 4,20 (m, 2H), 7,25 (m, 5H) |
| 10.06 | Propyl | Tetrahydrothiopyran-3-yl | — | 4,20 (m, 2H), 7,25 (m, 5H) |
| 10.07 | Ethyl | Tetrahydropyran-3-yl | 4-F | 3,90 (m, 2H), 4,17 (m, 2H), 6,93 (m, 2H), 7,13 (m, 2H) |
| 10.08 | Propyl | Tetrahydropyran-3-yl | 4-F | 3,90 (m, 2H), 4,17 (m, 2H), 6,93 (m, 2H), 7,13 (m, 2H) |
| 10.09 | Ethyl | Tetrahydropyran-4-yl | 4-F | |
| 10.10 | Propyl | Tetrahydropyran-4-yl | 4-F | |
| 10.11 | Ethyl | Tetrahydrothiopyran-3-yl | 4-F | 4,17 (m, 2H), 6,93 (m, 2H), 7,13 (m, 2H) |
| 10.12 | Propyl | Tetrahydrothiopyran-3-yl | 4-F | 4,17 (m, 2H), 6,93 (m, 2H), 7,13 (m, 2H) |
| 10.13 | Ethyl | Tetrahydropyran-3-yl | 4-Cl | 3,90 (m, 2H), 4,17 (m, 2H), 7,13 (m, 4H) |
| 10.14 | Propyl | Tetrahydropyran-3-yl | 4-Cl | 3,90 (m, 2H), 4,17 (m, 2H), 7,13 (m, 4H) |
| 10.15 | Ethyl | Tetrahydropyran-4-yl | 4-Cl | |
| 10.16 | Propyl | Tetrahydropyran-4-yl | 4-Cl | |
| 10.17 | Ethyl | Tetrahydrothiopyran-3-yl | 4-Cl | 4,17 (m, 2H), 7,13 (m, 4H) |
| 10.18 | Propyl | Tetrahydrothiopyran-3-yl | 4-Cl | 4,17 (m, 2H), 7,13 (m, 4H) |

TABLE 11

III ($R^e$ = —CH₂CH₂CH₂CH₂CH₂—O—[phenyl]—Radicals ; $R^g$, $R^h$, $R^i$ = H)

| No. | $R^d$ | $R^f$ | Radicals on phenyl ring | Phys. data/¹H-NMR [δ in ppm], mp. [°C.] |
|---|---|---|---|---|
| 11.01 | Ethyl | Tetrahydropyran-3-yl | — | 3,80–4,17 (m, 6H), 6,90 (m, 3H), 7,27 (m, 2H) |
| 11.02 | Propyl | Tetrahydropyran-3-yl | — | 3,80–4,17 (m, 6H), 6,90 (m, 3H), 7,27 (m, 2H) |
| 11.03 | Ethyl | Tetrahydropyran-4-yl | — | 3,90–4,17 (m, 6H), 6,90 (m, 3H), 7,27 (m, 2H) |
| 11.04 | Propyl | Tetrahydropyran-4-yl | — | 3,90–4,17 (m, 6H), 6,90 (m, 3H), 7,27 (m, 2H) |
| 11.05 | Ethyl | Tetrahydrothiopyran-3-yl | — | 3,97 (t, 2H), 4,07 (t, 2H), 6,90 (m, 3H), 7,27 (m, 2H) |
| 11.06 | Propyl | Tetrahydrothiopyran-3-yl | — | 3,97 (t, 2H), 4,07 (t, 2H), 6,90 (m, 3H), 7,27 (m, 2H) |
| 11.07 | Ethyl | Tetrahydropyran-3-yl | 4-F | 3,90 (m, 4H), 4,03 (t, 2H), 6,70–7,03 (m, 4H) |
| 11.08 | Propyl | Tetrahydropyran-3-yl | 4-F | 3,90 (m, 4H), 4,03 (t, 2H), 6,70–7,03 (m, 4H) |
| 11.09 | Ethyl | Tetrahydropyran-4-yl | 4-F | 3,83–4,13 (m, 6H), 6,70–7,03 (m, 4H) |
| 11.10 | Propyl | Tetrahydropyran-4-yl | 4-F | 3,83–4,13 (m, 6H), 6,70–7,03 (m, 4H) |
| 11.11 | Ethyl | Tetrahydrothiopyran-3-yl | 4-F | 3,90 (t, 2H), 4,03 (t, 2H) 6,70–7,03 (m, 4H) |
| 11.12 | Propyl | Tetrahydrothiopyran-3-yl | 4-F | 3,90 (t, 2H), 4,03 (t, 2H) 6,70–7,03 (m, 4H) |
| 11.13 | Ethyl | Tetrahydropyran-3-yl | 4-Cl | 3,80–4,10 (m, 6H), 6,80 (d, 2H), 7,20 (d, 2H) |
| 11.14 | Propyl | Tetrahydropyran-3-yl | 4-Cl | 3,80–4,10 (m, 6H), 6,80 (d, 2H), 7,20 (d, 2H) |
| 11.15 | Ethyl | Tetrahydropyran-4-yl | 4-Cl | 3,87–4,10 (m, 6H), 6,80 (d, 2H), 7,20 (d, 2H) |
| 11.16 | Propyl | Tetrahydropyran-4-yl | 4-Cl | 3,87–4,10 (m, 6H), 6,80 (d, 2H), 7,20 (d, 2H) |
| 11.17 | Ethyl | Tetrahydrothiopyran-3-yl | 4-Cl | 54–61 |
| 11.18 | Propyl | Tetrahydrothiopyran-3-yl | 4-Cl | 3,90 (t, 2H), 4,07 (t, 2H), 6,80 (d, 2H) |

TABLE 11-continued $R^f$ — cyclohexenone with OH, =NO—CH₂CH₂CH₂CH₂CH₂—O—phenyl (Radicals), $R^d$; III ($R^e$ = —CH₂CH₂CH₂CH₂CH₂—O—phenyl, Radicals; $R^g$, $R^h$, $R^i$ = H)

| No. | $R^d$ | $R^f$ | Radicals on phenyl ring | Phys. data/¹H-NMR [δ in ppm], mp. [°C.] |
|---|---|---|---|---|
| | | | | 7,20 (d, 2H) |

TABLE 12

Cyclohexenone with $OR^i$, =$NOR^e$, $R^d$, $R^f$, $R^g$, $R^h$; III

| No. | $R^d$ | $R^e$ | $R^f$ | $R^g$ | $R^h$ | $R^i$ | Reference |
|---|---|---|---|---|---|---|---|
| 12.1 | C₃H₇ | CH₂CH=CH₂ | CH₃ | CH₃ | CO₂CH₃ | Na | DE-A 2 439 104 |
| 12.2 | C₃H₇ | CH₂CH₃ | CH₂CH(CH₃)SCH₂CH₃ | H | H | H | DE-A 2 822 304 |
| 12.3 | C₂H₅ | CH₂CH=CHCl | CH₂CH(CH₃)SCH₂CH₃ | H | H | H | US-A 4 440 566 |
| 12.4 | C₃H₇ | CH₂CH=CHCl | CH₂CH(CH₃)SCH₂CH₃ | H | H | H | US-A 4 440 566 |
| 12.5 | C₃H₇ | C₂H₅ | 3-tetrahydrothiopyranyl | H | H | H | EP-A 71 707 |
| 12.6 | C₂H₅ | C₂H₅ | 3-tetrahydrothiopyranyl | H | H | H | EP-A 71 707 |
| 12.7 | CH₃ | CH₂CH=CHCH₃ | 3-tetrahydrothiopyranyl | H | H | H | EP-A 71 707 |
| 12.8 | C₃H₇ | C₂H₅ | 3-tetrahydropyranyl | H | H | H | EP-A 71 707 |
| 12.9 | C₂H₅ | CH₂CH=CHCl | 4-tetrahydropyranyl | H | H | H | EP-A 142 741 |
| 12.10 | C₃H₇ | C₂H₅ | 3-pyridyl | H | H | H | EP-A 66 195 |
| 12.11 | C₂H₅ | C₂H₅ | 4-methylphenyl | H | H | H | DE-A 24 39 104 |

TABLE 12-continued
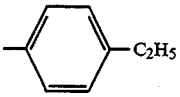
III
| No. | $R^d$ | $R^e$ | $R^f$ | $R^g$ | $R^h$ | $R^i$ | Reference |
|---|---|---|---|---|---|---|---|
| 12.12 | $C_2H_5$ | $CH_2CH=CHCH_3$ | 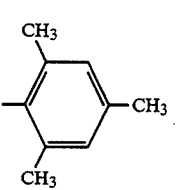 | H | H | H | DE-A 38 08 072 |
| 12.13 | $C_2H_5$ | $C_2H_5$ | 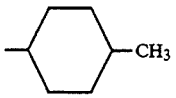 | H | H | H | EP-A 880 301 |
| 12.14 | $C_3H_7$ | $CH_2CH=CHCl$ | 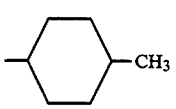 | H | H | H | EP-A 88 299 |
| 12.15 | $C_3H_7$ | $CH_2CH=CHCH_3$ | 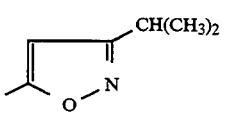 | H | H | H | EP-A 88 299 |
| 12.16 | $C_2H_5$ | $CH_2CH=CHCH_3$ | 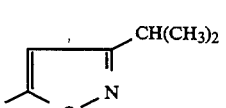 | H | H | H | EP-A 238 021 |
| 12.17 | $C_3H_7$ | $CH_2CH=CHCH_3$ | 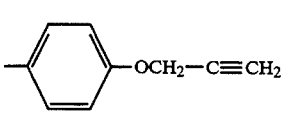 | H | H | H | EP-A 238 021 |
| 12.18 | $C_2H_5$ | $CH_2CH=CHCl$ | 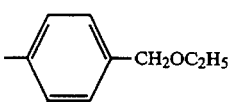 | H | H | H | EP-A 137 174 |
| 12.19 | $C_3H_7$ | $C_2H_5$ | 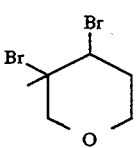 | H | H | H | EP-A 2 137 200 |
| 12.20 | $C_3H_7$ | $C_2H_5$ | 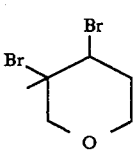 | H | H | H | EP-A 230 235 |
| 12.21 | $C_3H_7$ | $CH_2CH=CHCl$ |  | H | H | H | EP-A 230 235 |

TABLE 12-continued

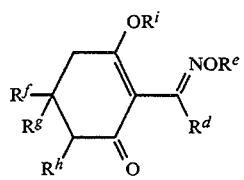

III

| No. | $R^d$ | $R^e$ | $R^f$ | $R^g$ | $R^h$ | $R^i$ | Reference |
|---|---|---|---|---|---|---|---|
| 12.22 | $C_3H_7$ | $CH_2CH=CHCl$ | 2,6,6-trimethylcyclohex-1-enyl | H | H | H | EP-A 46 860 |
| 12.23 | $C_3H_7$ | $C_2H_5$ | cyclohexyl | H | H | H | JP-A 540 191 945 |
| 12.24 | $C_3H_7$ | $C_2H_5$ | cyclohex-1-enyl | H | H | H | EP-A 46 860 |
| 12.25 | $CH_3$ | $CH_2CH=CHCl$ | 4-methylcyclohexyl | H | H | H | EP-A 88 299 |
| 12.26 | $C_3H_7$ | $C_2H_5$ | 4-($CF_3$)phenyl | H | H | K | EP-A 137 174 |
| 12.27 | $C_2H_5$ | $CH_2CH=CHCl$ | 2,6,6-trimethylcyclohex-1-enyl | H | H | H | EP-A 46 860 |
| 12.28 | $C_3H_7$ | $CH_2CH=CHCH_3$ | 2,4-dimethylthiazol-5-yl | H | H | H | EP-A 125 094 |
| 12.29 | $C_3H_7$ | $CH_2CH=CHCl$ | 2,4-dimethylthiazol-5-yl | H | H | H | EP-A 125 094 |
| 12.30 | $C_3H_7$ | $C_2H_5$ | 2,4,6-trimethylcyclohexyl | H | H | H | EP-A 88 299 |

TABLE 12-continued

III (Structure: cyclohexanone with $OR^i$, $=NOR^e$, $R^d$, $R^f$, $R^g$, $R^h$ substituents)

| No. | $R^d$ | $R^e$ | $R^f$ | $R^g$ | $R^h$ | $R^i$ | Reference |
|---|---|---|---|---|---|---|---|
| 12.31 | $C_3H_7$ | $CH_2CH=CH_2$ | (cyclohexyl with HO, H$_3$C, H$_5$C$_2$S substituents) | H | H | H | EP-A 228 598 |
| 12.32 | $C_2H_5$ | $C_2H_5$ | (cyclohexyl with two HO groups) | H | H | H | EP-A 228 598 |
| 12.33 | $C_3H_7$ | $C_2H_5$ | (1-methylpyrazol-3-yl) | H | H | H | EP-A 66 195 |
| 12.34 | $C_3H_7$ | $CH_2CH=CHCl$ | (1-methylpyrrol-3-yl) | H | H | H | EP-A 66195 |
| 12.35 | $C_3H_7$ | $CH_2CH=CH_2$ | (4-methyl-2-methylthiazoline) | H | H | H | EP-A 125 094 |
| 12.36 | $C_3H_7$ | $C_3H_7$ | $CH(SCH_2CH_3)_2$ | H | H | H | EP-A 230 260 |
| 12.37 | $C_3H_7$ | $C_2H_5$ | (tetrahydrothiopyran-S-oxide) | H | H | H | EP-A 115 808 |
| 12.38 | $C_3H_7$ | $C_2H_5$ | (tetrahydrothiopyran-S,S-dioxide) | H | H | H | EP-A 115 808 |
| 12.39 | $C_3H_7$ | $C_2H_5$ | $CH_3$ | $CH_3$ | $C(CH_3)=NOCH_3$ | H | EP-A 172 551 |
| 12.40 | $C_3H_7$ | $CH_2CH=CH_2$ | (tetrahydrothiopyran-S,S-dioxide) | OH | H | H | Proceedings Brit. Crop-Protection Conference - weeds 1985 Vol. 1 pages 93-98 |
| 12.41 | $C_2H_5$ | $CH_2CH=CH-CH_2-C_6H_4-Cl$ | (tetrahydrothiopyran) | H | H | H | EP-A 38 38 309 |

TABLE 12-continued

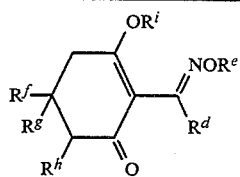

III

| No. | $R^d$ | $R^e$ | $R^f$ | $R^g$ | $R^h$ | $R^i$ | Reference |
|---|---|---|---|---|---|---|---|
| 12.42 | $C_2H_5$ | CH$_2$CH$_2$—CH=CH—(4-Cl-C$_6$H$_4$) | tetrahydrothiopyran-4-yl | H | H | H | EP-A 38 38 309 |
| 12.43 | $C_2H_5$ | CH$_2$CH$_2$—CH=CH—(4-F-C$_6$H$_4$) | tetrahydrothiopyran-4-yl | H | H | H | EP-A 38 38 309 |
| 12.44 | n-$C_3H_7$ | CH$_2$CH$_2$—CH=CH—(4-F-C$_6$H$_4$) | tetrahydrothiopyran-4-yl | H | H | H | EP-A 38 38 309 |
| 12.45 | $C_2H_5$ | CH$_2$CH=CH—CH$_2$—C$_6$H$_5$ | tetrahydrothiopyran-4-yl | H | H | H | EP-A 38 38 309 |
| 12.46 | n-$C_3H_7$ | CH$_2$-(5-Cl-thien-2-yl) | tetrahydrothiopyran-4-yl | H | H | H | EP-A 177 913 |
| 12.47 | $C_2H_5$ | CH$_2$-(5-Cl-thien-2-yl) | tetrahydrothiopyran-4-yl | H | H | H | EP-A 177 913 |
| 12.48 | $C_2H_5$ | CH$_2$-(5-Cl-thien-2-yl) | tetrahydropyran-4-yl | H | H | H | EP-A 177 913 |
| 12.49 | n-$C_3H_7$ | CH$_2$-(5-Cl-thien-2-yl) | tetrahydropyran-4-yl | H | H | H | EP-A 177 913 |
| 12.50 | n-$C_3H_7$ | CH$_2$-(thien-2-yl) | tetrahydrothiopyran-4-yl | H | H | H | EP-A 177 913 |
| 12.51 | $CH_3$ | CH$_2$-(thien-2-yl) | tetrahydropyran-4-yl | H | H | H | EP-A 177 913 |
| 12.52 | $C_2H_5$ | CH$_2$-(thien-2-yl) | tetrahydropyran-4-yl | H | H | H | EP-A 177 913 |

TABLE 13
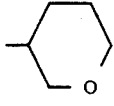
(R$^e$ = —CH$_2$(CH$_2$)$_2$CH$_2$— 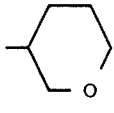 ; R$^g$, R$^h$, R$^i$ = H)
| No. | R$^d$ | R$^f$ | Radicals on phenyl ring | Physical data [NMR* (δ in ppm)] |
|---|---|---|---|---|
| 13.01 | C$_2$H$_5$ | 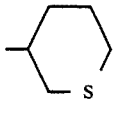 | 4-F | 2.9 (broad, 2H); 4.1 (broad, 2H) |
| 13.02 | n-C$_3$H$_7$ | 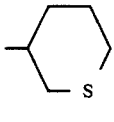 | 4-F | 2.9 (t, 2H); 4.05 (broad, 2H) |
| 13.03 | C$_2$H$_5$ | 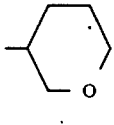 | 4-F | 2.9 (t, 2H); 4.05 (broad, 2H) |
| 13.04 | n-C$_3$H$_7$ | 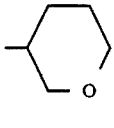 | 4-F | 2.9 (t, 2H); 4.05 (broad, 2H) |
| 13.05 | C$_2$H$_5$ | 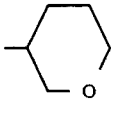 | 4-F | 4.05 (broad, 2H) |
| 13.06 | n-C$_3$H$_7$ | 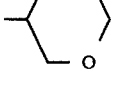 | 4-F | 4.05 (broad, 2H) |
| 13.07 | C$_2$H$_5$ | 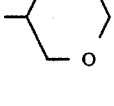 | 4-Cl | 2.9 (t, 2H); 4.05 (broad, 2H) |
| 13.08 | n-C$_3$H$_7$ | 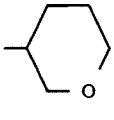 | 4-Cl | 2.9 (t, 2H); 4.05 (broad, 2H) |
| 13.09 | C$_2$H$_5$ | | 4-Cl | 2.9 (t, 2H); 4.05 (broad, 2H) |
| 13.10 | n-C$_3$H$_7$ | | 4-Cl | 2.9 (broad, 2H); 4.05 (broad, 2H) |

TABLE 13-continued

Radicals III

[Structure: cyclohexenone with OH, R^f substituent, =N-O-(CH2)4-phenyl with Radicals, R^d substituent, =O]

(R^e = —CH2(CH2)2CH2—phenyl—Radicals ; R^g, R^h, R^i = H)

| No. | R^d | R^f | Radicals on phenyl ring | Physical data [NMR* (δ in ppm)] |
|---|---|---|---|---|
| 13.11 | C2H5 | [tetrahydrothiopyran] | 4-Cl | 4.05 (broad, 2H) |
| 13.12 | n-C3H7 | [tetrahydrothiopyran] | 4-Cl | 4.05 (broad, 2H) |

*selected signals

Herbicidal active ingredients and antidote compounds can be applied together or separately, after emergence, to the leaves and shoots of the crops and of the undesirable grasses. The antidote is preferably applied simultaneously with the herbicidal active ingredient. Separate application, where the antidote is first applied to the field and then the herbicidal active ingredient, is also possible. The herbicidal active ingredient and the antidote can be formulated together or separately as a spray in suspendable, emulsifiable or soluble form.

Antidote effects are also achieved by treating the seeds of crops or the seedlings with the antidote before sowing or before planting out. The herbicidal active ingredient is then applied alone in the conventional manner.

In the treatment of seeds, in general from 0.1 to 10 g, preferably from 1 to 2 g, of active ingredient are required per kilogram of seed.

In the application of the antidote by seed swelling or in the treatment of seedlings, solutions which contain the antagonistic active ingredient in a concentration of from 1 to 10,000 ppm, in particular from 100 to 10,000 ppm, are preferably used.

Different amounts of an antidote compound are required for herbicidal (hetaryloxy)- or aryloxyphenoxyacetic acid derivatives II if the herbicide is used in different crops. The ratios can be varied within wide ranges. They are likewise dependent on the structure of the (hetaryloxy)- or aryloxyphenoxyacetic acid derivatives and on the particular target crop. Suitable weight ratios of herbicidal active ingredients to antidote compound are from 1:10 to 1:0.01, preferably from 1:4 to 1:0.1.

Different amounts of an antidote compound are required for the same cyclohexenone derivative III if the latter is used in different crops. The ratios in which the cyclohexenone derivative and a substituted 2-aminothiophene I are used can be varied within wide ranges. They are dependent on the structure of the cyclohexenone derivative and of the substituted 2-aminothiophene I and on the particular crop. Suitable weight ratios of herbicidal active ingredient to antidote compound are from 1:10 to 1:0.01, preferably from 1:4 to 1:0.25.

The novel agents or, in the case of separate applications, the herbicidal active ingredients or the antidote are applied, for example in the form of directly sprayable solutions, powders, suspensions, including concentrated aqueous, oily or other suspensions, or dispersions, emulsions, oil dispersions, pastes, dusting agents, broadcasting agents or granules, by spraying, atomizing, dusting, broadcasting or pouring. The application forms depend entirely on the intended uses.

Mineral oil fractions having a medium to high boiling point, such as kerosene or diesel oil, as well as coal tar oils and oils of vegetable or animal origin, aliphatic, cyclic or aromatic hydrocarbons, e.g. benzene, toluene, xylene, paraffin, tetrahydronaphthalene, alkylated naphthalenes or derivatives thereof, for example methanol, ethanol, propanol, butanol, chloroform, carbon tetrachloride, cyclohexanol, cyclohexanone, chlorobenzene or isophorone, and strongly polar solvents, e.g. dimethylformamide, dimethyl sulfoxide, N-methylpyrrolidone and water, are suitable for the preparation of directly sprayable solutions, emulsions, pastes and oil dispersions.

Aqueous application forms can be prepared from emulsion concentrates, pastes, wettable powders or oil dispersions by adding water. For the preparation of emulsions, pastes or oil dispersions, the herbicidal active ingredient and/or the antidote, as such or in solution in an oil or solvent, are homogenized in water by means of wetting agents, adherents, dispersants or emulsifiers. However, it is also possible to prepare concentrates which consist, in addition to the herbicidal active ingredient and/or the antidote, of wetting agents, adherents, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkyl sulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensates of sulfonated naphthalene and naphthalene derivatives with formaldehyde, condensates of naphthalene or of naphthalenesulfonic acids with phenol and formaldehyde, polyoxyethylene octylphenol ethers, ethoxylated isooctylphenol, octylphenol and nonylphenol, alkylphenol polyglycol ethers, tributylphenol polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin sulfite waste liquors and methylcellulose.

Powders, broadcasting agents and dusting agents can be prepared by mixing or milling the herbicidal active ingredient and/or the antidote together with a solid carrier.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, chalk, talc, bole, loess, clay, dolomite, kieselguhr, calcium sulfate, magnesium sulfate, magnesium oxide, milled plastics, fertilizers, e.g. ammonium sulfate, ammonium phosphate, ammonium nitrate and ureas, and vegetable products, such as grain flours, bark meal, wood meal and nutshell meal, cellulosic powders and others.

The formulations contain from 0.01 to 95, preferably from 0.5 to 90, % by weight of herbicidal active ingredient and antidote. The application rates of herbicidal active ingredient are from 0.05 to 5 kg of active substance (a.s.) per hectare.

The novel herbicides may contain, in addition to the substituted 2-aminothiophene I as the antidote and the herbicide from the group consisting of the (hetaryloxy)- or aryloxyphenoxyacetic acids II or of the cyclohexenones III, further herbicidal or growth-regulating active ingredients having a different chemical structure, the antagonistic effect being retained.

PREPARATION EXAMPLES

EXAMPLE 1

2-Benzoylamino-3-cyano-4,5,6,7-tetrahydrobenzo[b]thiophene

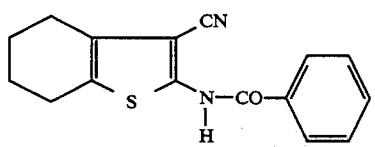

4.7 ml (40 mmol) of benzoyl chloride were added to a solution of 5.34 g (30 mmol) of 2-amino-3-cyano-4,5,6,7-tetrahydrobenzo[b]thiophene in 50 ml of pyridine. Stirring was carried out for 2 hours at 80° C. after which 150 ml of 10 mol % aqueous hydrochloric acid were added to the mixture. The solid formed was isolated in a conventional manner. Yield: 97%; mp.: 168°–170° C.

Intermediate 1α

2-Amino-3-cyano-4,5,6,7-tetrahydrobenzo[b]thiophene

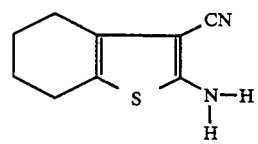

200 ml (2.3 mol) of morpholine were slowly added at about 20° C. to a mixture of 200 g (2.0 mol) of cyclohexanone, 132 g (2.0 mol) of malonodinitrile, 64 g (2.0 mol) of sulfur and 800 ml of ethanol. Stirring was carried out for four hours, after which the solid formed was isolated in a conventional manner. Yield: 51%; mp.: 40°–141° C.

EXAMPLE 2

2-(3,4-Dichloromaleimino-1-yl)-3-cyano-4,5,6,7-tetrahydrobenzo[b]thiophene[sic]

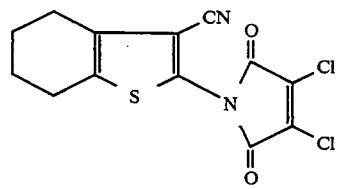

A mixture of 8.9 g (50 mmol) of 2-amino-3-cyano-4,5,6,7-tetrahydrobenzo[b]thiophene (prepared according to Intermediate 1e), 8.4 g (50 mmol) of 3,4-dichloromaleic anhydride and 100 ml of glacial acetic acid was refluxed for two hours. After the mixture had been cooled, the product which had crystallized out was isolated in a conventional manner. Yield: 85%; mp.: 155°–60° C.

EXAMPLE 3

2-(3-n-Butylureido)-3-cyano-4,5,6,7-tetrahydrobenzo[b]thiophene

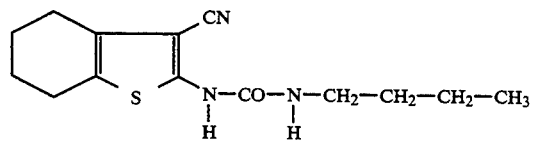

A mixture of 5.35 g (30 mmol) of 2-amino-3-cyano-4,5,6,7-tetrahydrobenzo[b]thiophene (prepared according to Intermediate 1e), 2.0 ml (45 mmol) of triethylamine, 10 ml (90 mmol) of n-butyl isocyanate and 100 ml of toluene was stirred for 16 hours at 80° C. The solid formed was then isolated and was recrystallized from ethanol. Yield: 18%; mp.: 170°–171° C.

EXAMPLE 4

2-(2,4-Dichlorophenylmethanimino)-3-cyano-4,5,6,7-tetrahydrobenzo[b]thiophene

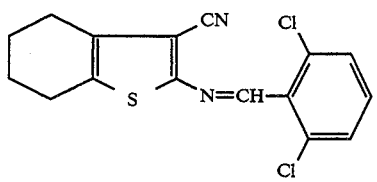

A mixture of 8.9 g (50 mmol) of 2-amino-3-cyano-4,5,6,7-tetrahydrobenzo[b]thiophene (prepared according to Intermediate 1e), 8.8 g (50 mmol) of 2,6-dichlorobenzaldehyde, 0.2 g (1.1 mmol) of p-toluenesulfonic acid and 150 ml of toluene was heated at the boiling point for hours with continuous removal of the resulting water of reaction. After the reaction mixture had been cooled, the product which had crystallized out was isolated in a conventional manner. Yield: 65%; mp.: 182°–183° C.

EXAMPLE 5

2-Acylamino-3-cyano-4,5-benzo-6,7-dihydrobenzo[b]thiophene

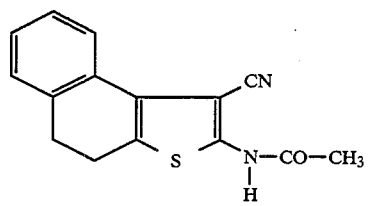

A solution of 13.56 g (60 mmol) of 2-amino-3-cyano-4,5-benzo-6,7-dihydrobenzo[b]thiophene in 100 ml of acetic anhydride was refluxed for 4 hours. After cooling to about 20° C., the reaction mixture was poured into 50 ml of water and was neutralized with 80 ml of concentrated ammonia solution. The crystalline product was then isolated in a conventional manner. Yield: 69%; mp.: 60°–263° C.

Intermediate 5a

2-Amino-3-cyano-4,5-benzo-6,7-dihydrobenzo[b]thiophene

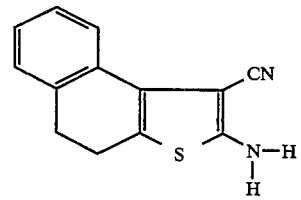

A mixture of 292 g (2.0 mol) of α-tetralone, 132 g (2.0 mol) of malononitrile, 16 g (0.2 mol) of ammonium acetate, 50 ml of glacial acetic acid and 800 ml of toluene was heated at the boiling point for 4 hours with continuous removal of the resulting water of reaction and was then extracted by shaking with 200 ml of water. Thereafter, the solvent was removed and 900 ml of ethanol, 49.5 g (1.5 mol) of sulfur and 155 ml (1.5 mol) of diethylamine were added to the residue. The resulting mixture was heated at 60° C. for 90 minutes, after which the product crystallized out on cooling. Yield: 64%; mp. 164°–166° C.

Further compounds I, which were prepared, or can be prepared, by similar methods, are shown in Tables 14 and 15 below.

TABLE 14

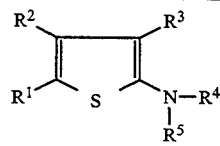

I

| No. | $R^1$ | $R^2$ | $R^3$ | $R^4$ | $R^5$ | mp. [°C.] |
|---|---|---|---|---|---|---|
| 14.01 | $C_6H_5$ | H | CN | H | H | |
| 14.02 | $CH_2$—$CH_3$ | H | CN | H | H | |
| 14.03 | $CH_2$—$CH_3$ | H | CO—$NH_2$ | H | H | |
| 14.04 | —$(CH_2)_4$— | | CN | CO—$CH_2$—$C_2H_5$ | H | 125–130 |
| 14.05 | —$(CH_2)_4$— | | CN | CO—$(CH_2)_{14}$—$CH_3$ | H | |
| 14.06 | —$(CH_2)_4$— | | CN | CO—$C(CH_3)_3$ | H | 167–170 |
| 14.07 | —$(CH_2)_4$— | | CN | CO—$CH_2$—$C(CH_3)_3$ | H | 167–170 |
| 14.08 | —$(CH_2)_4$— | | CN | CO—$CH_2Cl$ | H | |
| 14.09 | —$(CH_2)_4$— | | CN | CO—$CCl_3$ | H | |
| 14.10 | —$(CH_2)_4$— | | CN | CO—$CF_3$ | H | |
| 14.11 | —$(CH_2)_4$— | | CN | CO—⟨cyclohexyl⟩ | H | |
| 14.12 | —$(CH_2)_4$— | | CN | CO—$CH_2$—$C_6H_5$ | H | |
| 14.13 | —$(CH_2)_4$— | | CN | CO—(2-Cl—$C_6H_4$) | H | 143–156 |
| 14.14 | —$(CH_2)_4$— | | CN | CO—(4-Cl—$C_6H_4$) | H | 126–130 |
| 14.15 | —$(CH_2)_4$— | | CN | CO—(2,4-$Cl_2$—$C_6H_4$) | H | 170 (decomposition) |
| 14.16 | —$(CH_2)_4$— | | CN | CO—(2-$NO_2$—$C_6H_4$) | H | 215–217 |
| 14.17 | —$(CH_2)_4$— | | CN | CO—(3-$NO_2$—$C_6H_4$) | H | |
| 14.18 | —$(CH_2)_4$— | | CN | CO—(4-$NO_2$—$C_6H_4$) | H | |
| 14.19 | —$(CH_2)_4$— | | CN | $SO_2$—$CH_3$ | H | |
| 14.20 | —$(CH_2)_4$— | | CN | $SO_2$—$C_6H_5$ | H | |

TABLE 14-continued

Structure I:
R² and R³ on thiophene ring; R¹ attached to S-bearing carbon; N(R⁴)(R⁵) on the other carbon adjacent to S.

| No. | R¹ | R² | R³ | R⁴ | R⁵ | mp. [°C.] |
|---|---|---|---|---|---|---|
| 14.21 | —(CH₂)₄— | | CN | SO₂—(4-CH₃—C₆H₄) | H | 115–120 |
| 14.22 | —(CH₂)₄— | | CN | CO—NH₂ | H | 176–180 |
| 14.23 | —(CH₂)₄— | | CN | CO—NH—(3,4-Cl₂—C₆H₃) | H | >240 |
| 14.24 | —(CH₂)₄— | | CN | CO—NH—CO₂—NH—C₆H₅ | H | |
| 14.25 | —(CH₂)₄— | | CN | CO—NH—SO₂—N(morpholino) | H | 70–75 |
| 14.26 | —(CH₂)₄— | | CN | CO—NH—SO₂—N(piperidino) | H | 65–70 |
| 14.27 | —(CH₂)₄— | | CN | CO—NH—SO₂—N(4-methylpiperazin-1-yl) | H | 207–210 |
| 14.28 | —(CH₂)₄— | | CN | CO—NH—SO₂—N(C₆H₁₁)₂ | H | >240 |
| 14.29 | —(CH₂)₄— | | CN | CO—NH—SO₂—NH—C₆H₁₁ | H | 138 (decomposition) |
| 14.30 | —(CH₂)₄— | | CN | CS—NH—C₆H₅ | H | 170–180 |
| 14.31 | —(CH₂)₄— | | CN | CS—NH—CO—(2-NO₂—C₆H₄) | H | |
| 14.32 | —(CH₂)₄— | | CN | CS—NH—CO—(3-NO₂—C₆H₄) | H | 195–197 |
| 14.33 | —(CH₂)₄— | | CN | CS—NH—CO—(4-NO₂—C₆H₄) | H | 211–215 |
| 14.34 | —(CH₂)₄— | | CN | CS—NH—CO—(2-Cl—C₆H₄) | H | 183–186 |
| 14.35 | —(CH₂)₄— | | CN | CS—NH—CO—(4-Cl—C₆H₄) | H | 218–222 |
| 14.36 | —(CH₂)₄— | | CN | PO(OC₆H₅)₂ | H | oil |
| 14.37 | —(CH₂)₄— | | CN | PO(OC₂H₅)₂ | H | oil |
| 14.38 | —(CH₂)₄— | | CN | 2,4-(NO₂)₂—C₆H₃ | H | 140–144 |
| 14.39 | —(CH₂)₄— | | CN | =C(NH₂)₂ | | 198–205 |
| 14.40 | —(CH₂)₄— | | CN | =C(NH—C₆H₁₁)₂ | | 120–127 |
| 14.41 | —(CH₂)₄— | | CN | =CH—NH₂ | | 203 |
| 14.42 | —(CH₂)₄— | | CN | =CH—C₆H₅ | | 116–117 |
| 14.43 | —(CH₂)₄— | | CN | =CH—(2-Cl—C₆H₄) | | 142–146 |
| 14.44 | —(CH₂)₄— | | CN | =CH—(2,3-Cl₂—C₆H₃) | | 211–213 |
| 14.45 | —(CH₂)₄— | | CN | =CH—(2,6-Cl₂—C₆H₃) | | 182–183 |
| 14.46 | —(CH₂)₄— | | CN | =CH—(3,4-Cl₂—C₆H₃) | | 192–193 |
| 14.47 | —(CH₂)₄— | | CN | =CH—(4-NO₂—C₆H₄) | | 180–182 |
| 14.48 | —(CH₂)₄— | | CN | =CH—(4-pyridyl) | | 146–151 |
| 14.49 | —(CH₂)₄— | | CN | =CH(CN)₂ | | 105–110 |
| 14.50 | —(CH₂)₄— | | CO—NH₂ | CO—C₂H₅ | H | 131–136 |
| 14.51 | —(CH₂)₄— | | CO—NH₂ | CO—C(CH₃)₃ | H | 172–175 |
| 14.52 | —(CH₂)₄— | | CO—NH₂ | CO—(2-NO₂—C₆H₄) | H | 313–317 |
| 14.53 | —(CH₂)₄— | | CO—NH₂ | CO—(3-NO₂—C₆H₄) | H | |

TABLE 14-continued $$\begin{array}{c} R^2 \quad R^3 \\ \diagdown \diagup \\ \| \quad \| \\ R^1 - \text{S} - \text{N} - R^4 \\ \quad\quad\quad | \\ \quad\quad\quad R^5 \end{array}$$ I

| No. | $R^1$ | $R^2$ | $R^3$ | $R^4$ | $R^5$ | mp. [°C.] |
|---|---|---|---|---|---|---|
| 14.54 | —(CH$_2$)$_4$— | | CN | —CO—(1,2-C$_6$H$_4$)—CO— (phthaloyl) | | 220–221 |
| 14.55 | —(CH$_2$)$_4$— | | CN | —CO—(4-cyclohexenyl-1,2-diyl)—CO— | | 125–130 |
| 14.56 | —(CH$_2$)$_4$— | | CN | —CO—(cyclohexenyl-1,2-diyl)—CO— | | 112–116 |
| 14.57 | —(CH$_2$)$_4$— | | CN | —CO—CH$_2$—CH$_2$—CO— | | |
| 14.58 | —(CH$_2$)$_4$— | | CN | —CO—CH=CH—CO— | | |
| 14.59 | —(CH$_2$)$_4$— | | CN | —CO—CCl=CCl—CO— | | 115–160 |
| 14.60 | —(CH$_2$)$_2$—(2-C$_6$H$_4$)— | | CN | COCH$_3$ | H | 259–262 |
| 14.61 | —(CH$_2$)$_2$—(2-C$_6$H$_4$)— | | CN | CO—C$_2$H$_5$ | H | 220 |
| 14.62 | —(CH$_2$)$_2$—(2-C$_6$H$_4$)— | | CN | CO—C(CH$_2$)$_3$ | H | 163–165 |
| 14.63 | —(CH$_2$)$_2$—(2-C$_6$H$_4$)— | | CN | CO—CH$_2$—C(CH$_3$)$_3$ | H | 235–239 |
| 14.64 | —(CH$_2$)$_2$—(2-C$_6$H$_4$)— | | CN | CO—C$_6$H$_5$ | H | 188–193 |
| 14.65 | —(CH$_2$)$_2$—(2-C$_6$H$_4$)— | | CN | CO—(2-Cl—C$_6$H$_4$) | H | 176–178 |

TABLE 14-continued

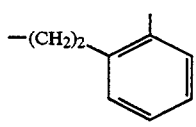

| No. | R¹ | R² | R³ | R⁴ | R⁵ | mp. [°C.] |
|---|---|---|---|---|---|---|
| 14.66 | —(CH₂)₂—[2-CH₃-C₆H₄] | | CN | CO—(2,4-Cl₂—C₆H₃) | H | 175–177 |
| 14.67 | —(CH₂)₂—[2-CH₃-C₆H₄] | | CN | SO₂—(4-CH₃—C₆H₄) | H | 200–203 |
| 14.68 | —(CH₂)₂—[2-CH₃-C₆H₄] | | CN | CO—NH—(CH₂)₃—CH₃ | H | 218–222 |
| 14.69 | —(CH₂)₂—[2-CH₃-C₆H₄] | | CN | CO—NH—C₆H₅ | H | >250 |
| 14.70 | —(CH₂)₂—[2-CH₃-C₆H₄] | | CN | CO—NH—(3,4-Cl₂—C₆H₃) | H | 250–255 |
| 14.71 | —(CH₂)₂—[2-CH₃-C₆H₄] | | CN | —CO—CH=CH—CO— | | >250 |
| 14.72 | —(CH₂)₂—[2-CH₃-C₆H₄] | | CN | —CO—CCl=CCl—CO— | | 208–213 |

TABLE 15

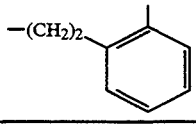

| No. | R¹ | R² | R³ | R⁴ | R⁵ | mp. [°C.] | Reference |
|---|---|---|---|---|---|---|---|
| 15.001 | CH₃ | CH₃ | CN | H | H | 141–142 | [1] |
| 15.002 | CO—OCH₂H₅ | CH₃ | CO—OC₂H₅ | H | H | 108–111 | [1] |
| 15.003 | C₆H₅ | CH₃ | CO—OC₂H₅ | H | H | 95 | [1] |
| 15.004 | C₆H₅ | H | CO—OC₂H₅ | H | H | 123–124 | [1] |
| 15.005 | C₆H₅ | H | CO—NH₂ | H | H | 218–220 | [1] |
| 15.006 | H | C₆H₅ | CO—OC₂H₅ | H | H | 98 | [1] |
| 15.007 | C₂H₅ | H | CO—OC₂H₅ | H | H | 73 | [1] |
| 15.008 | —(CH₂)₄— | | CN | H | H | 147–148 | [1] |
| 15.009 | —(CH₂)₄— | | CO—NH₂ | H | H | 189–190 | [1] |
| 15.010 | —(CH₂)₄— | | CO—OC₂H₅ | H | H | 115 | [1] |

TABLE 15-continued

Structure I: thiophene with R¹ at 2-position, R² at 3-position, R³ at 4-position, and N(R⁴)(R⁵) at 5-position.

| No. | R¹ | R² | R³ | R⁴ | R⁵ | mp. [°C.] | Reference |
|---|---|---|---|---|---|---|---|
| 15.011 | | —(CH₂)₂—(2-methylphenyl) | CN | H | H | 165–168 | [2] |
| 15.012 | | —(CH₂)₄— | CN | CO—CH₃ | H | 216–217 | |
| 15.013 | | —(CH₂)₄— | CN | CO—C₂H₅ | H | 181–182 | |
| 15.014 | | —(CH₂)₄— | CN | CO—(CH₂)₂—Cl | H | 176–179 | |
| 15.015 | | —(CH₂)₄— | CN | CO—(CH₂)₃—Cl | H | 143–146 | |
| 15.016 | | —(CH₂)₄— | CN | CO—C₆H₅ | H | 168–170 | |
| 15.017 | | —(CH₂)₄— | CN | CO—NH—CH₃ | H | | |
| 15.018 | | —(CH₂)₄— | CN | CO—NH—(CH₂)₃—CH₃ | H | 170–171 | |
| 15.019 | | —(CH₂)₄— | CN | CO—NH—cyclohexyl | H | 201–211 | |
| 15.020 | | —(CH₂)₄— | CN | CO—NH—C₆H₅ | H | >240 | |
| 15.021 | | —(CH₂)₄— | CN | CS—NH—CO—C₆H₅ | H | 196–202 | |
| 15.022 | | —(CH₂)₄— | CN | —CH=CH—CH=CH— | | 91–92 | |
| 15.023 | | —(CH₂)₄— | CN | =CH—(4-Cl—C₆H₄) | | 142–146 | |
| 15.024 | | —(CH₂)₄— | COOH | H | H | 132–134 | |
| 15.024 | | —(CH₂)₄— | CO—NH₂ | CO—CH₃ | H | 170–174 | |
| 15.025 | | —(CH₂)₄— | CO—NH₂ | CO—(4-NO₂—C₆H₄) | H | 187–190 | |
| 15.026 | | —(CH₂)₄— | CO—OC₂H₅ | CO—CH₃ | H | 121–122 | |
| 15.027 | | —(CH₂)₄— | CO—OC₂H₅ | CO—NH₂ | H | 203–213 | |
| 15.028 | | H | CH₃ | CO—OCH₃ | H | H | |
| 15.029 | | H | C₆H₅ | CN | H | H | |
| 15.030 | | —(CH₂)₃— | CO—NH₂ | H | H | | |
| 15.031 | | —(CH₂)₄— | CO—OCH(CH₃)₂ | H | H | | |
| 15.032 | | —(CH₂)₄— | CN | =CH—N(CH₃)₂ | | | |
| 15.033 | | —(CH₂)₄— | CO—NH₂ | =CH—N(CH₃)₂ | | | |
| 15.034 | H | CH₃ | COOH | H | H | | |
| 15.035 | | —(CH₂)₄— | COOH | CO—NH₂ | H | | |
| 15.036 | | —(CH₂)₄— | COOH | CO—NHCH₃ | H | | |
| 15.037 | | —(CH₂)₄— | COOH | CO—N(CH₃)₂ | H | | |
| 15.038 | | —(CH₂)₄— | COOH | CO—NH—CH(CH₃)₂ | H | | |
| 15.039 | | —(CH₂)₃— | CN | H | H | | |
| 15.040 | CO—CH₃ | CH₃ | CN | H | H | | |
| 15.041 | CO—OC₂H₅ | CH₃ | CN | H | H | | |
| 15.042 | | —(CH₂)₄— | CO—NH₂ | —CO—CCl=CCl—CO— | | | |
| 15.043 | | —(CH₂)₄— | CO—OCH₃ | H | H | | |
| 15.044 | | —(CH₂)₄— | CO—OC₂H₅ | CO—NH—CH₃ | H | | |
| 15.045 | | —(CH₂)₄— | CO—OC₂H₅ | CO—NH—CH(CH₃)₂ | H | | |
| 15.046 | CH₃ | CH₃ | CO—NH₂ | H | H | | |
| 15.047 | H | CH₃ | CO—OC₂H₅ | H | H | | |
| 15.048 | | —(CH₂)₄— | CN | CO—NH—CH(CH₃)₂ | H | | |
| 15.049 | H | H | CO—OCH₃ | H | H | 77–78 | [3] |
| 15.050 | H | H | CO—NH₂ | H | H | | |
| 15.051 | CH₃ | H | CO—NH₂ | H | H | | |
| 15.052 | H | H | CO—NH—CH(CH₃)₂ | H | H | | |
| 15.053 | CH₃ | H | CO—NH—CH(CH₃)₂ | H | H | | |
| 15.054 | H | C₆H₅ | CO—OCH₃ | H | H | | |
| 15.055 | H | 4-CH₃O—C₆H₄ | CO—OCH₃ | H | H | | |
| 15.056 | CO—OCH₃ | CH₃ | CN | H | H | | |
| 15.057 | | —(CH₂)₄— | CO—OC₂H₅ | CO—NH(CH₃)₂ | H | | |
| 15.058 | H | 4-Cl—C₆H₄ | CN | H | H | | |
| 15.059 | H | H | CN | H | H | 104–105 | [3] |
| 15.060 | H | CH₃ | CO—NH₂ | H | H | 176–178 | [3] |
| 15.061 | CH₃ | H | CO—OC₂H₅ | H | H | 46 | [1] |
| 15.062 | | —(CH₂)₄— | CN | CO—CH=CH₂ | H | 135 | |

TABLE 15-continued

I

| No. | R$^1$ | R$^2$ | R$^3$ | R$^4$ | R$^5$ | mp. [°C.] | Reference |
|---|---|---|---|---|---|---|---|
| 15.063 | | —(CH$_2$)$_2$—(o-C$_6$H$_4$)— | CN | —CO—(cyclohexane-1,2-diyl)—CO— | | | |
| 15.064 | | —(CH$_2$)$_2$—(o-C$_6$H$_4$)— | CN | —PO(OC$_6$H$_5$)$_2$ | H | oil | |
| 15.065 | | —(CH$_2$)$_2$—(o-C$_6$H$_4$)— | CN | —PO(OC$_2$H$_5$)$_2$ | H | oil | |
| 15.066 | H | CH$_3$ | CN | H | H | 119–120 | [3] |
| 15.067 | | —(CH$_2$)$_4$— | CN | CO—NH—SO$_2$—N(piperidino) | H | 65–70 | |
| 15.068 | | —(CH$_2$)$_4$— | CO—NH$_2$ | =C(NH—cyclohexyl)$_2$ | | 88–91 | |
| 15.069 | | —(CH$_2$)$_4$— | CO—NH$_2$ | CO—(2,4-Cl$_2$—C$_6$H$_3$) | H | | |
| 15.070 | | —(CH$_2$)$_4$— | CO—OC$_2$H$_5$ | CO—(4-Cl—C$_6$H$_4$) | H | 165–168 | |
| 15.071 | | —(CH$_2$)$_4$— | CO—OC$_2$H$_5$ | CO—(2,4-Cl$_2$—C$_6$H$_3$) | H | 165–168 | |
| 15.072 | | —(CH$_2$)$_4$— | CN | =CH—NH—S—(cyclohexyl with CN) | | | |
| 15.073 | | —(CH$_2$)$_4$— | CO—NH$_2$ | =CH—NH—S—(cyclohexyl with C(O)NH$_2$) | | | |
| 15.074 | | —(CH$_2$)$_4$— | | —CO—O—CO— | H | | |
| 15.075 | | —(CH$_2$)$_4$— | CO—OC$_2$H$_5$ | SO$_2$—NH—CH(CH$_3$)$_2$ | H | | |
| 15.076 | | —(CH$_2$)$_4$— | CO—NH$_2$ | CO—CF$_3$ | H | | |
| 15.077 | | —(CH$_2$)$_4$— | CN | SO$_2$—NH—CH(CH$_3$)$_2$ | H | | |
| 15.078 | | —(CH$_2$)$_4$— | CN | SO$_2$—NH—CH$_3$ | H | | |
| 15.079 | CN | CH$_3$ | CO—OCH$_3$ | H | H | | |
| 15.080 | CN | CH$_3$ | COOH | H | H | | |
| 15.081 | | —CH$_2$—N(CH$_3$)—(CH$_2$)$_2$— | CN | H | H | | |
| 15.082 | | —CH$_2$—N(CH$_3$)—(CH$_2$)$_2$— | CO—OC$_2$H$_5$ | H | H | | |
| 15.083 | H | H | CO—NH—C$_6$H$_5$ | H | H | | |
| 15.084 | | —CH$_2$—[N(CH$_3$)$_2$Br]—(CH$_2$)$_2$— | CO—OC$_2$H$_5$ | H | H | | |
| 15.085 | CN | CH$_3$ | CN | H | H | | |
| 15.086 | CN | CH$_3$ | CO—OC$_2$H$_5$ | H | H | | |
| 15.087 | CO—N(CH$_2$H$_5$)$_2$ | CH$_3$ | CN | H | H | | |
| 15.088 | CO—NH—[2,4-(CH$_3$O)$_2$-5-Cl—C$_6$H$_5$] | CH$_3$ | CN | H | H | | |

TABLE 15-continued

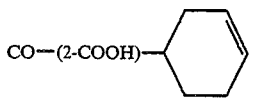

| No. | R¹ | R² | R³ | R⁴ | R⁵ | mp. [°C.] | Reference |
|---|---|---|---|---|---|---|---|
| 15.089 | | —CO—N($C_6H_5$)—CO— | CN | H | H | | |
| 15.090 | | —CO—NH—CO— | CN | H | H | | |
| 15.091 | CN | $CHCl_2$ | CN | H | H | | |
| 15.092 | CO—$OC_2H_5$ | CO—$OC_2H_5$ | CN | H | H | | |
| 15.093 | CO—$OCH_3$ | COOH | CN | H | H | | |
| 15.094 | CO—$OCH_3$ | CO—$OCH_3$ | CN | H | H | | |
| 15.095 | CO—O($CH_2$)$_2$—$OCH_3$ | $CH_3$ | CN | H | H | | |
| 15.096 | | —($CH_2$)$_4$— | CO—$OC_2H_5$ | (2,6-$NO_2$, 3-Cl, 4-$CH_3$)—$C_6H_1$ | H | | |
| 15.097 | | —($CH_2$)$_4$— | CO—$OC_2H_5$ | (2,6-$NO_2$, 4-$CF_3$)—$C_6H_2$ | H | | |
| 15.098 | | —C($CH_3$)$_2$—O—C($CH_3$)$_2$— | CN | H | H | | |
| 15.099 | | —($CH_2$)$_4$— | CN | CO—(2-COOH)— | H | | |
| 15.100 | | —($CH_2$)$_4$— | CN | 2,6-$Cl_2$-Triazin-2-yl | H | | |
| 15.101 | | —($CH_2$)$_4$— | CN | CO—NH—$SO_2$—N⟨ ⟩ | H | 238 (decomposition) | |
| 15.102 | | —($CH_2$)$_4$— | CN | CO—NH—$SO_2$—N⟨ ⟩O | H | 70-75 | |
| 15.103 | | —($CH_2$)$_4$— | CN | CS—NH—COO$CH_3$ | H | | |
| 15.104 | | —($CH_2$)$_4$— | CO—$OC_2H_5$ | CS—NH—COO$CH_3$ | H | | |
| 15.105 | | —($CH_2$)$_4$— | CN | C($CH_3$)=CH—CO$CH_3$ | H | 134-137 | |
| 15.106 | | —($CH_2$)$_4$— | C($NH_2$)=N—(4-Cl—$C_6H_4$) | H | H | 152-160 | |
| 15.107 | | —($CH_2$)$_4$— | C($NH_3$Cl)=N—(4-Cl—$C_6H_4$) | H | H | | |
| 15.108 | | —($CH_2$)$_4$— | CO—$NH_2$ | CO—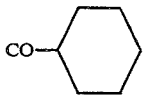 | H | 140-146 | |

References:
[1] K. Gewald et al., Chem. Ber. 99 (1966), 94
[2] E. C. Taylor et at., J. Org. Chem. 32 (1967), 2376
[3] . Gewald, Chem. Ber. 98 (1965), 3571

EXAMPLES OF BIOLOGICAL ACTION

The effect of various novel herbicides or herbicide combinations, consisting of the herbicide and the antidote, on the growth of desired and undesirable plants in comparison with the herbicidal active ingredient alone is demonstrated by the following biological examples from greenhouse experiments:

In greenhouse experiments, the culture vessels used were plastic flowerpots having a capacity of about 300 cm³ and containing loamy sand and about 3.0% of humus as a substrate. The seeds of the test plants were sown shallowly and separately according to species and were moistened. The vessels were then covered with transparent plastic covers until the seeds had uniformly germinated and the plants had begun to grow.

List of Test Plants

| Botanical name | Common name |
|---|---|
| Setaria viridis | green foxtail |
| Triticum aestivum | wheat |
| Zea mays | Indian corn |

For the postemergence treatment, the test plants were first grown to a height of from 3 to 20 cm, depending on the form of growth, before being treated. The herbicides were suspended or emulsified in water as a distributing agent and sprayed by means of finely distributing nozzles.

The following was used as an example of the herbicidal cyclohexenone derivatives of the formula III:

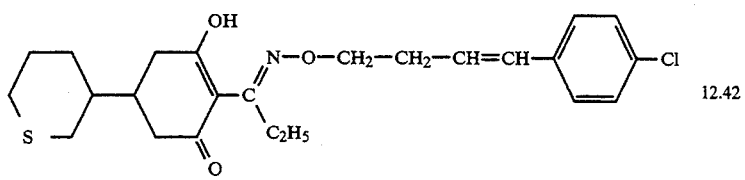

12.42

For the postemergence treatment, all antidote compounds were prepared in a mixture consisting of 80% by weight of cyclohexenone as a solvent and 20% by weight of a surfactant (Emulphor EL*)) with 10% by weight of active ingredient.
*) Ethoxylated castor oil For comparison, the herbicidal active ingredient 12.42 was formulated as a 10–20% strength by weight emulsion concentrate and was used in the spray liquor in each case with the addition of the amount of solvent system with which the antidote compound was applied at the application rates shown in the Tables. The solution was prepared by mixing the active ingredient into a solution of 93% by weight of xylene and 7% by weight of Lutensol ® AP-8**).
**) Nonionic surfactant based on alkylphenol polyethylene glycol ethers After application of the active ingredient mixture, the test plants were cultivated in a greenhouse, warmth-loving species at about 18°–30° C. and those from more temperate climates at about 10°–25° C.

The test period extended over from 3 to 5 weeks. During this time, the plants were tended and their reaction to the individual treatments was recorded.

The damage by the chemical agents was evaluated on the basis of a scale from 0 to 100% in comparison with the untreated control plants. 0 means no damage and 100 means complete destruction of the plants.

Table 16 documents the antidote action of the novel example compounds No. 14.14, 14.38, 15,014, 15.019, 15.020, 15,022, 15,027 and 15,062.

TABLE 16

Improvement of the toleration of the herbicide 12.42 by corn as a result of admixing an antidote example compound in postemergence application; greenhouse experiment

| Antidote No. | Application rate [kg/ha a.s.] Herbicide | Antidote | Test plants and damage [%] Crop Corn | Undesirable plant Seteria viridis |
|---|---|---|---|---|
| — | 0.125 | — | 85 | 100 |
| 15.019 | 0.125 | 0.125 | 25 | 95 |
| 15.020 | 0.125 | 0.125 | 20 | 80 |
| 15.062 | 0.125 | 0.125 | 25 | 90 |
| 14.14 | 0.125 | 0.125 | 30 | 100 |
| 15.014 | 0.125 | 0.125 | 30 | 90 |
| — | 0.06 | — | 60 | 95 |
| 15.027 | 0.06 | 0.06 | 30 | 80 |
| 15.022 | 0.06 | 0.06 | 25 | 70 |
| 14.38 | 0.06 | 0.06 | 15 | 70 |

Table 16 shows that the substituted 2-aminothiophenes substantially increase the toleration of the herbicide 12.42 by crops from the Gramineae family (grasses).

We claim:

1. A herbicidal composition containing one or more substituted 2-aminothiophenes of the formula I

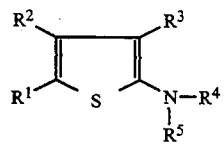

where
R$^1$ and R$^2$ together form a C$_4$-alkylene chain to which a benzene ring may be fused,
R$^3$ is —CN or CX—R$^6$, where X is oxygen or sulfur and, where R$^6$ is hydroxyl, C$_1$–C$_4$-alkoxy or amino,
R$^4$ is hydrogen or a phenyl group which may carry one or two nitro radicals, or —PO(OR$^8$)$_2$, —CX—R$^9$, —SO$_2$R$^{10}$ or —CX—N(H)—CO—R$^8$
where
X is oxygen or sulfur;
R$^8$ is hydrogen, C$_1$–C$_4$-alkyl or a phenyl group;
R$^9$ is C$_1$–C$_{20}$-alkyl, partially or completely halogenated C$_1$–C$_6$-alkyl, C$_2$–C$_6$-alkenyl, C$_6$-cycloalkyl, or amino, C$_1$–C$_4$-alkylamino, C$_3$–C$_8$-cycloalkylamino, phenyl or phenylamino, where the aromatic moiety may each carry one or two halogen atoms and/or one nitro radical;
R$^{10}$ is C$_1$–C$_4$-alkyl or phenyl, which may carry one C$_1$–C$_4$-alkyl radical;
R$^5$ is hydrogen;
or
R$^4$ and R$^5$ together form a —CH=CH—CH=CH— group;
and the basic salts of the compounds I in which R$^3$ is hydroxycarbonyl or hydroxythiocarbonyl, and the acidic salts of the compounds I which contain a basic nitrogen atom, as antagonistic compounds and one or more herbicidal active ingredients from the group consisting of the cyclohexenone derivatives of the formula III

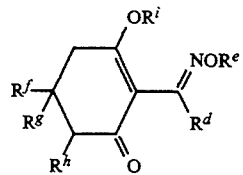

where
R$^d$ is C$_1$–C$_4$-alkyl;
R$^e$ is C$_1$–C$_4$-alkyl, C$_3$- or C$_4$-alkenyl, C$_3$- or C$_4$-alkynyl or partially or completely halogenated C$_3$- or C$_4$-alkenyl;
a C$_1$–C$_4$-alkylene or C$_1$–C$_4$-alkenylene chain, both of which may furthermore carry one C$_1$–C$_3$-alkyl radical or one halogen atom, or a 3-membered to 6-membered alkylene or 4-membered to 6-membered alkenylene chain which is, if desired, substituted by C$_1$–C$_3$-alkyl and each of which contains, as a chain member, an oxygen or sulfur atom which is not directly adjacent to the oxime ether moiety, all abovementioned chains carrying a terminal phenyl ring which in turn may be substituted by from one to three radicals selected from a group consisting of nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl; or $R^e$ is thienylmethyl which may carry a halogen atom;

$R^f$ is $C_1$–$C_4$-alkyl which may be monosubstituted by $C_1$–$C_4$-alkylthio; a 6-membered saturated ring system which, in addition to carbon members, may contain an oxygen or sulfur atom;

or phenyl which may carry from one to three of the following radicals: $C_1$–$C_4$-alkyl, $R^g$ is hydrogen or, when $R^f$ is $C_1$–$C_6$-alkyl is $C_1$–$C_6$-alkyl;

$R^h$ is hydrogen, and $R^i$ is hydrogen or one equivalent of an agriculturally useful cation.

2. A herbicidal composition as claimed in claim 1, containing a substituted 2-aminothiophene I as an antagonistic compound and a herbicide III in a weight ratio of from 0.01:1 to 10:1.

3. A method for selectively controlling undesirable plant growth, wherein a substituted 2-aminothiophene I, as an antagonistic compound, and a cyclohexenone derivative of the formula III as claimed in claim 1 are applied, simultaneously or in succession, before, during or after sowing of the crops or before or during emergence of the crops.

4. A method for selectively controlling undesirable plant growth, wherein the leaves of the crops and of the undesirable plants are treated simultaneously or in succession, by the postemergence method, with a substituted 2-aminothiophene I, as an antagonistic compound, and with a cyclohexenone derivative of the formula III as claimed in claim 1.

5. A method for preventing damage to crops by herbicidal cyclohexenone derivatives of the formula III as claimed in claim 1, wherein the seed of the crops is treated with an antagonistic amount of a substituted w-aminothiophene of the formula I as claimed in claim 1.

6. A method as claimed in claim 4, wherein the crops are barley, wheat, corn, sorghum or rice.

7. A method as claimed in claim 5, wherein the crops are barley, wheat, corn, sorghum or rice.

8. A method as claimed in claim 3, wherein the crops are barley, wheat, corn sorghum and rice.

* * * * *

UNITED STATES PATENT AND TRADEMARK OFFICE
CERTIFICATE OF CORRECTION

PATENT NO.: 5,422,335

DATED: June 6, 1995

INVENTOR(S): HAGEN et al.

It is certified that error appears in the above-identified patent and that said Letters Patent is hereby corrected as shown below:

In the Abstract, line 2 after formula I, delete "from" and substitute --form--.

In the Abstract, second page, delete the formula III presently shown and substitute the following:

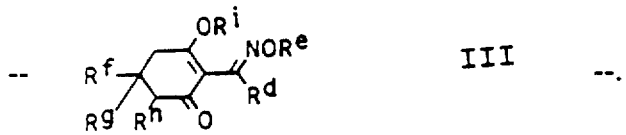

Signed and Sealed this

Third Day of October, 1995

Attest:

BRUCE LEHMAN

Attesting Officer

Commissioner of Patents and Trademarks